United States Patent
Barvian et al.

(10) Patent No.: US 6,686,355 B2
(45) Date of Patent: Feb. 3, 2004

(54) BIPHENYL SULFONAMIDES USEFUL AS MATRIX METALLOPROTEINASE INHIBITORS

(75) Inventors: Nicole Chantel Barvian, Ann Arbor, MI (US); Patrick Michael O'Brien, Stockbridge, MI (US); William Chester Patt, Chelsea, MI (US); Drago Robert Sliskovic, Saline, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 24 days.

(21) Appl. No.: 10/074,667

(22) Filed: Feb. 13, 2002

(65) Prior Publication Data

US 2002/0156074 A1 Oct. 24, 2002

Related U.S. Application Data

(60) Provisional application No. 60/268,755, filed on Feb. 14, 2001.

(51) Int. Cl.$^7$ .................... C07D 279/12; C07D 417/12; A61K 31/541; A61K 31/54; A61P 19/02
(52) U.S. Cl. .................. 514/227.5; 546/58.2; 546/58.4; 514/228.2
(58) Field of Search ............................ 544/58.2, 58.4; 514/227.5, 228.2

(56) References Cited

U.S. PATENT DOCUMENTS

| | | | |
|---|---|---|---|
| 5,948,780 A | 9/1999 | Peterson, Jr. et al. | 514/255 |
| 6,008,243 A | 12/1999 | Bender et al. | 514/422 |

FOREIGN PATENT DOCUMENTS

| | | |
|---|---|---|
| EP | 1 081 137 A1 | 3/2001 |
| WO | WO 96/33172 | 10/1996 |
| WO | WO 97/20824 | 6/1997 |
| WO | WO 97/44315 | 11/1997 |
| WO | WO 98/08822 | 3/1998 |
| WO | WO 98/34918 * | 8/1998 |
| WO | WO 00/09492 | 2/2000 |
| WO | WO 01/63244 A1 | 8/2001 |

OTHER PUBLICATIONS

Robert A. Greenwald {Annals of New York Academy of Sciences 878:413–419 (1999)}.*
Skiles et al. {Annual Reports in Medicinal Chemisty–36, Chapter 15, pp. 167–176, 2000}.*
Coussens et al. {Science vol. 295, Mar. 29, pp. 2387–2392, (2002)}.*
Skiles et al. {Current Medicinal Chemistry, 8, 425–474 (2001)}.*
D R Close {Ann. Rheum. Dis 60, pp. iii62–iii67 (2002)}.*
Jackson et al. {Inflamma. Res 50, 183–186 (2001)}.*
Montana, John, et al, "The design of selective non–substrate–based matrix metalloproteinase inhibitors", Current Opinion in Drug Discovery & Development, 2000; 3(4), pp 353–361.
Clark, Ian, et al, "Matrix metalloproteinase inhibitors in the treatment of arthritis", Current Opinions in Anti–inflammatory & Immunomodulatory Investigational Drugs, 2000; 2(1), pp 16–25.
Chen, James, et al, "Structure–Based Design of a Novel, Potent, and Selective Inhibitor for MMP–13 Utilizing NMR Spectroscopy and Computer–Aided Molecular Design", J. Am. Chem. Soc., 2000, 122; pp 9648–9654.
Derwent Abstract, 2000—301906/32.
Derwent Abstract, 97–332465/30.
Derwent Abstract, 98–447147/38.
Derwent Abstract, 96–485703/48.
Derwent Abstract, 2000–205958/18.
European Search Report for EP 02 00 2814.
Almstead, Neil G., et al, "Design, Synthesis, and Biological Evaluation of Potent Thiazine– and Thiazepine–Based Matrix Metalloproteinase Inhibitors", J. Med. Chem., 1999, 42, pp 4547–4562 XP–000919158.

* cited by examiner

Primary Examiner—Mark L. Berch
Assistant Examiner—Kahsay Habte
(74) Attorney, Agent, or Firm—Charles W. Ashbrook; Claude F. Purchase, Jr.

(57) ABSTRACT

Inhibitors of MMP enzymes are cyclic sulfonamides of Formula I

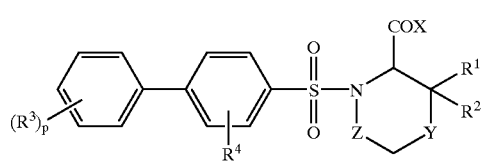

or a pharmaceutically acceptable salt thereof, and cyclic sulfonamides of Formula III

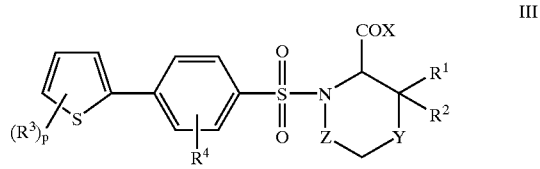

or a pharmaceutically acceptable salt thereof,
wherein $R^1$ and $R^2$ include hydrogen, alkyl, and substituted alkyl; $R^3$ and $R^4$ include hydrogen, halo, and alkyl; X is OH or NHOH; Z is $(CH_2)_n$; and Y is S, SO or $SO_2$. The compounds of Formulas I and III are useful for the treatment of diseases mediated by an MMP enzyme, including cancer, osteoarthritis, rheumatoid arthritis, heart failure, and inflammation.

28 Claims, No Drawings

BIPHENYL SULFONAMIDES USEFUL AS MATRIX METALLOPROTEINASE INHIBITORS

CROSS-REFERENCE TO RELATED APPLICATIONS

This application claims benefit of priority from U.S. provisional patent application No. 60/268,755, filed Feb. 14, 2001.

FIELD OF THE INVENTION

This invention relates to a group of biphenyl sulfonamide compounds and derivatives which inhibit matrix metalloproteinase enzymes and thus are useful for treating diseases resulting from connective tissue breakdown, such as heart disease, multiple sclerosis, arthritis, atherosclerosis, and osteoporosis.

BACKGROUND OF THE INVENTION

Matrix metalloproteinases (sometimes referred to as MMPs) are naturally-occurring enzymes found in most mammals. Over-expression and activation of MMPs or an imbalance between MMPs and inhibitors of MMPs have been suggested as factors in the pathogenesis of diseases characterized by the breakdown of extracellular matrix or connective tissues.

Stromelysin-1 and gelatinase A are members of the matrix metalloproteinases (MMP) family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., and Seiki M., *Nature*, 1994;370:61–65). These enzymes have been implicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting metalloproteinase enzymes, thereby curtailing and/or eliminating the breakdown of connective tissues that results in the disease states.

The catalytic zinc in matrix metalloproteinases is typically the focal point for inhibitor design. The modification of substrates by introducing zinc chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation. MMP inhibitors have also been used to prevent and treat congestive heart failure and other cardiovascular diseases, U.S. Pat. No. 5,948,780.

There is a need to discover new low molecular weight compounds that are potent inhibitors of MMP enzymes without causing undesired side effects in animals. McClure recently described a series of arylsulfonyl hydroxamic acid derivatives that are said to be useful as broad spectrum MMP inhibitors (see WO 98/34918). We now have discovered a series of biphenyl sulfonamides that are especially potent MMP inhibitors with little or no toxic effects.

SUMMARY OF THE INVENTION

In a preferred embodiment, this invention provides a group of cyclic sulfonamide compounds that are inhibitors of matrix metalloproteinase enzymes, and especially MMP-2, -3, -9, -12, -13, and -14. The invention is more particularly directed to compounds defined by Formula I

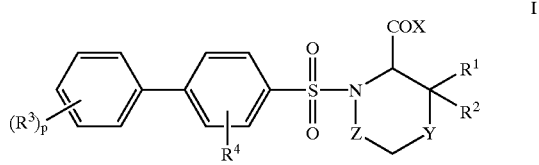

Or a pharmaceutically acceptable salt thereof,
wherein:
Each $R^1$ and $R^2$ independently are hydrogen or $C_1$–$C_6$ alkyl;
Z is $(CH_2)_n$;
each $R^3$ and $R^4$ independently are hydrogen, halo, $C_1$–$C_6$ alkyl, $C_2$–$C_6$ alkenyl, $C_2$–$C_6$ alkynyl; $(CH_2)_m$ OH, $(CH_2)_m$ $OR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m$ $NR^5R^6$, $(CH_2)_m$ $COR^5$, $(CH_2)_m$ $CONR^5R^6$, or $(CH_2)_m$ $CO_2R^5$, $NO_2$, phenoxy, CN, CHO;
or two $R^3$ groups on adjacent carbon atoms may be taken together with the carbon atoms to which they are attached to form a ring diradical selected from:

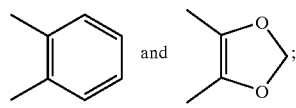

$R^5$ and $R^6$ independently are hydrogen or $C_1$–$C_6$ alkyl, or $R^5$ and $R^6$ taken together with the nitrogen atom to which they are attached complete a 3- to 7-membered ring containing carbon atoms, the nitrogen atom, and optionally 1 heteroatom selected from O, S, and $NR^1$, wherein $R^1$ is as defined above;
is an integer of from 0 to 3;
m is an integer of from 0 to 6;
n is 0, 1, or 2;
Y is S, SO, or $SO_2$; and
X is OH or NHOH.
Preferred compounds have Formula I wherein $R^4$ is hydrogen or fluoro.
A preferred group of compounds have Formula II

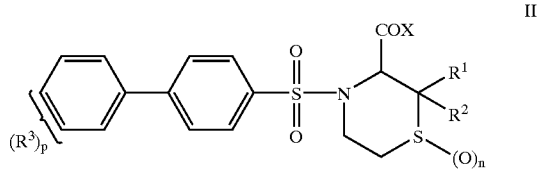

Wherein $R^1$, $R^2$, $R^3$, n, p, and X are as defined above.
Especially preferred compounds have Formula II wherein $R^3$ is halo, particularly bromo or iodo.
An especially preferred group of compounds have Formula I wherein $R^3$ is alkyl substituted with amino, alkylamino, or dialkylamino. Illustrative examples include aminomethyl, 2-dimethylamino-ethyl, and 3-methylaminobutyl.

Further preferred compounds are those of Formula II, wherein two $R^3$ groups on adjacent carbon atoms are taken together with the carbon atoms to which they are attached to form a ring diradical selected from and Further preferred compounds are those of Formulas I or II wherein X is OH.

Still further preferred compounds have Formulas I or II wherein X is NHOH.

Another embodiment of this invention is a pharmaceutical composition, comprising a compound of Formula I, or a pharmaceutically acceptable salt thereof, admixed with a pharmaceutically acceptable carrier, excipient, or diluent. Preferred compositions comprise compounds of Formula II, or a pharmaceutically acceptable salt thereof.

Another embodiment of this invention is a method for inhibiting an MMP enzyme, comprising administering to a mammal an MMP enzyme inhibiting amount of a compound of Formula I, or a pharmaceutically acceptable salt thereof.

Another embodiment of this invention is a method for treating a disease mediated by an MMP enzyme, comprising administering to a patient suffering from such a disease an effective amount of a compound of Formula I, or a pharmaceutically acceptable salt thereof. Preferred methods comprise administering a compound having Formula II, or a pharmaceutically acceptable salt thereof.

A preferred method of treatment according to this invention is treatment of a disease selected from: cancer, especially breast carcinoma, inflammation, heart failure, osteoarthritis, and rheumatoid arthritis.

Another embodiment of the present invention is a compound of Formula III

III

Or a pharmaceutically acceptable salt thereof,
  wherein:
    Each $R^1$ and $R^2$ independently are hydrogen or $C_1-C_6$ alkyl;
    Z is $(CH_2)_n$;
    each $R^3$ and $R^4$ independently are hydrogen, halo, $C_1-C_6$ alkyl, $C_2-C_6$ alkenyl, $C_2-C_6$ alkynyl, $(CH_2)_m$ OH, $(CH_2)_m$ $OR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle, $(CH_2)_m$ $NR^5R^6$, $(CH_2)_m$ $COR^5$, $(CH_2)_m$ $CONR^5R^6$, or $(CH_2)_m$ $CO_2R^5$, $NO_2$, phenoxy, CN, CHO;
    or two $R^3$ groups on adjacent carbon atoms may be taken together with the carbon atoms to which they are attached to form a ring diradical selected from:

and $R^5$ and $R^6$ independently are hydrogen or $C_1-C_6$ alkyl, or taken together with the nitrogen to which they are attached complete a 3- to 7-membered ring containing carbon atoms, the nitrogen atom, and optionally 1 heteroatom selected from O, S, and $NR^1$, wherein $R^1$ is as defined above;
p is an integer of from 0 to 3;
m is an integer of from 0 to 6;
n is 0, 1, or 2;
Y is S, SO, or $SO_2$; and
X is OH or NHOH.

A preferred group of compounds have Formula IV

IV

Or a pharmaceutically acceptable salt thereof,
  wherein:
    Each $R^1$ and $R^2$ independently are hydrogen or $C_1-C_6$ alkyl;
    each $R^3$ independently is hydrogen, halo, $C_1-C_6$ alkyl, $C_2-C_6$ alkenyl, $C_2-C_6$ alkynyl, $(CH_2)_m$ OH, $(CH_2)_m$ $OR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle, $(CH_2)_m$ $NR^5R^6$, $(CH_2)_m$ $COR^5$, $(CH_2)_m$ $CONR^5R^6$, or $(CH_2)_m$ $C_2R^5$, $NO_2$, phenoxy, CN, CHO;
    or two $R^3$ groups on adjacent carbon atoms may be taken together with the carbon atoms to which they are attached to form a ring diradical selected from:

and $R^5$ and $R^6$ independently are hydrogen or $C_1-C_6$ alkyl, or taken together with the nitrogen to which they are attached complete a 3- to 7-membered ring containing carbon atoms, the nitrogen atom, and optionally 1 heteroatom selected from O, S, and $NR^1$, wherein $R^1$ is as defined above;
m is an integer of from 0 to 6;
p is an integer from 1 to 5;
n is 0, 1, or 2; and
X is OH or NHOH.

Especially preferred compounds have Formula III wherein $R^3$ is halo, particularly chloro.

An especially preferred group of compounds have Formula III wherein $R^3$ is alkyl substituted with amino, alkylamino, or dialkylamino. Illustrative examples include aminomethyl, 2-dimethylamino-ethyl, and 3-methylamino-butyl.

Further preferred compounds are those of Formulas III or IV wherein X is OH.

Still further preferred compounds have Formulas III or IV wherein X is NHOH.

Another embodiment of this invention is a pharmaceutical composition, comprising a compound of Formula III, or a pharmaceutically acceptable salt thereof, admixed with a pharmaceutically acceptable carrier, excipient, or diluent. Preferred compositions comprise compounds of Formula IV, or a pharmaceutically acceptable salt thereof.

Another embodiment of this invention is a method for inhibiting an MMP enzyme, comprising administering to a mammal an MMP enzyme inhibiting amount of a compound of Formula III, or a pharmaceutically acceptable salt thereof.

Another embodiment of this invention is a method for treating a disease mediated by an MMP enzyme, comprising administering to a patient suffering from such a disease an effective amount of a compound of Formula III, or a pharmaceutically acceptable salt thereof. Preferred methods comprise administering a compound having Formula IV, or a pharmaceutically acceptable salt thereof.

A preferred embodiment of this invention is a method of treating a disease selected from: cancer, especially breast carcinoma, inflammation, heart failure, osteoarthritis, and rheumatoid arthritis, comprising administering to a mammal in need of treatment an effective amount of a compound selected from a compound of Formula I, II, III, or IV, or a pharmaceutically acceptable salt thereof.

Another embodiment of the present invention is a method for treating a disease mediated by an MMP enzyme, comprising administering to a patient suffering from such a disease an effective amount of a combination of 2 or 3 compounds independently selected from Formula I, II, III, or IV, or a pharmaceutically acceptable salt thereof.

DETAILED DESCRIPTION OF THE INVENTION

The compounds provided by this invention are those defined by Formula I. In Formula I, $R^1$–$R^4$ include "$C_1$–$C_6$ alkyl" groups. These are straight and branched carbon chains having from 1 to 6 carbon atoms. Examples of such alkyl groups include methyl, ethyl, isopropyl, tert.-butyl, neopentyl, and n-hexyl. The alkyl groups can be substituted if desired, for instance with groups such as hydroxy, amino, alkylamino, and dialkylamino, halo, trifluoromethyl, carboxy, nitro, and cyano.

Examples of $NR^5R^6$ groups include amino, methyl amino, di-isopropylamino, acetyl amino, propionyl amino, 3-aminopropyl amino, 3-ethylaminobutyl amino, 3-di-n-propylamino-propyl amino, 4-diethylaminobutyl amino, and 3-carboxypropionyl amino. $R^5$ and $R^6$ can be taken together with the nitrogen to which they are attached to form a ring containing 3 to 7 carbon atoms and 1, 2, or 3 heteroatoms selected from the group consisting of nitrogen, substituted nitrogen, oxygen, and sulfur. Examples of such cyclic $NR^5R^6$ groups include pyrrolidinyl, piperazinyl, 4-methylpiperazinyl, 4-benzylpiperazinyl, pyridinyl, piperidinyl, pyrazinyl, morpholinyl, and the like.

"Halo" includes fluoro, chloro, bromo, and iodo.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl", which means a cycloalkyl group also bearing at least one heteroatom selected from O, S, or N $R^1$, wherein $R^1$ is as defined above, examples being oxiranyl, pyrrolidinyl, piperidyl, tetrahydropyran, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as —O—$(CH_2)_2$—O—$OH_3$, and the like.

"Alkanoyl" groups are alkyl linked through a carbonyl, ie, $C_1$-$C_5$—C(O)—. Such groups include formyl, acetyl, propionyl, butyryl, and isobutyryl.

"Acyl" means an R group that is an alkyl or aryl (Ar) group bonded through a carbonyl group, i.e., R—C(O)—. For example, acyl includes a $C_1$-$C_6$ alkanoyl, including substituted alkanoyl, wherein the alkyl portion can be substituted by $NR^5R^6$ or a carboxylic or heterocyclic group. Typical acyl groups include acetyl, benzoyl, and the like.

The alkyl, alkenyl, alkoxy, and alkynyl groups described above are optionally substituted, preferably by 1 to 3 groups selected from $NR^5R^6$, $CONR^5R^6$, $COC_1$—$C_6$ alkyl, phenyl, substituted phenyl, thio $C_1$–$C_6$ alkyl, $C_1$–$C_6$ alkoxy, hydroxy, carboxy, $C_1$–$C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph where n is 1, 2, or 3. Perhalo and polyhalo substitution is also embraced.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanyl-methyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxhexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidyl-butyl, 3-imidazolidin-1-ylpropyl, 4-tetrahydrothiazol-3-yl-butyl, phenylmethyl, 3-chlorophenylmethyl, and the like.

The terms "Ar" and "aryl" refer to unsubstituted and substituted aromatic groups. Heteroaryl groups have from 4 to 9 ring atoms, from 1 to 4 of which are independently selected from the group consisting of O, S, and N. Preferred heteroaryl groups have 1 or 2 heteroatoms in a 5- or 6-membered aromatic ring. Mono and bicyclic aromatic ring systems are included in the definition of aryl and heteroaryl. Typical aryl and heteroaryl groups include phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, morpholinyl, indolyl, benzotriazolyl, indazolyl, pyrrolyl, pyrazolyl, imidazolyl, thiazolyl, thiophenyl, and the like.

Preferred Ar groups are phenyl and phenyl substituted by 1, 2, or 3 groups independently selected from the group consisting of alkyl, alkoxy, thio, thioalkyl, halo, hydroxy, $-COOR^7$, trifluoromethyl, nitro, amino of the formula $-NR^5R^6$, and $T(CH_2)_mQR^4$ or $T(CH_2)_mCO_2R^4$ wherein m is 1 to 6, T is O, S, $NR^4$, $N(O)R^4$, $NR^4R^6Y$, or $CR^4R^5$, Q is O, S, $NR^5$, $N(O)R^5$, or $NR^5R^6Y$ wherein $R^4$ and $R^5$ are as described above, and $R^7$ is alkyl or substituted alkyl, for example, methyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl, methoxy, chloro, methyl, $NO_2$, phenoxy, CN, and CHO.

Two $R^3$ groups on adjacent carbon atoms may be taken together with the carbon atoms to which they are attached to form a ring diradical selected from

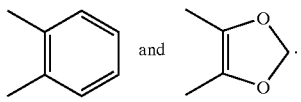

Examples 28, 33, and 36 below illustrate this embodiment.

The phrase "LC purity" means the percent amount of a compound in a sample being analyzed by high performance liquid chromatography.

The phrase "MS APCI" means the mass-to-charge value for a compound's parent molecular ion, or for the compound's parent molecular ion-hydrogen adduct as determined by positive ion atmospheric pressure chemical ionization mass spectrometry.

The term "patient" means a mammal. Preferred patients include humans, cats, dogs, cows, horses, pigs, and sheep.

The term "animal" means a mammal. Preferred animals include humans, rats, mice, guinea pigs, rabbits, monkeys, cats, dogs, cows, horses, pigs, and sheep.

The term "cancer" as used herein includes all types of solid tumor diseases including colon cancer, breast cancer, lung cancer, prostate cancer, cancer of the oral cavity and pharynx, cancer of the stomach, small intestine, large intestine, rectum, liver, bone, connective tissue, skin, ovary, testis, bladder, kidney, brain, the central nervous system, and the like.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the United States Food and Drug Administration, or an equivalent foreign agency.

The phrase "anticancer effective amount" means an amount of invention compound, or a pharmaceutically acceptable salt thereof, sufficient to inhibit, halt, or cause regression of the cancer being treated in a particular patient or patient population. For example in humans or other mammals, an anticancer effective amount can be determined experimentally in a laboratory or clinical setting, or may be the amount required by the guidelines of the United States Food and Drug Administration, or equivalent foreign agency, for the particular cancer and patient being treated.

The phrase "MMP enzyme inhibiting amount" means an amount of invention compound, or a pharmaceutically acceptable salt thereof, sufficient to inhibit a matrix metalloproteinase enzyme, including a truncated form thereof, including a catalytic domain thereof, in a particular animal or animal population. For example in a human or other mammal, an MMP inhibiting amount can be determined experimentally in a laboratory or clinical setting, or may be the amount required by the guidelines of the United States Food and Drug Administration, or equivalent foreign agency, for the particular MMP enzyme and patient being treated.

It should be appreciated that the matrix metalloproteinases include the following enzymes:

MMP-1, also known as interstitial collagenase, collagenase-1, or fibroblast-type collagenase;

MMP-2, also known as gelatinase A or 72 kDa Type IV collagenase;

MMP-3, also known as stromelysin or stromelysin-1;

MMP-7, also known as matrilysin or PUMP-1;

MMP-8, also known as collagenase-2, neutrophil collagenase, or polymorphonuclear-type ("PMN-type") collagenase;

MMP-9, also known as gelatinase B or 92 kDa Type IV collagenase;

MMP-10, also known as stromelysin-2;

MMP-11, also known as stromelysin-3;

MMP-12, also known as metalloelastase;

MMP-13, also known as collagenase-3;

MMP-14, also known as membrane-type ("MT") 1-MMP or MT1-MMP;

MMP-15, also known as MT2-MMP;

MMP-16, also known as MT3-MMP;

MMP-17, also known as MT4-MMP;

MMP-18; and

MMP-19.

Other MMPs are known, including MMP-26, which is also known as matrilysin-2.

It should be appreciated that determination of proper dosage forms, dosage amounts, and routes of administration, is within the level of ordinary skill in the pharmaceutical and medical arts, and is described below.

The term "$IC_{50}$" means the concentration of test compound required to inhibit activity of a biological target, such as a receptor or enzyme, by 50%.

The phrase "catalytic domain" means the domain containing a catalytic zinc cation of the MMP enzyme, wherein the MMP enzyme contains two or more domains. A catalytic domain includes truncated forms thereof that retain at least some of the catalytic activity of the MMP or MMP-CD. For example, the collagenases, of which MMP-1, MMP-8, and MMP-13 are members, have been reported to contain a signal peptide domain, a propeptide domain, a catalytic domain, and a hemopexin-like domain (Ye Qi-Zhuang, Hupe D., Johnson L., *Current Medicinal Chemistry*, 1996;3:407–418).

The phrase "a method for inhibiting an MMP enzyme" includes methods of inhibiting a full-length MMP, truncated forms thereof that retain catalytic activity, including forms that contain the catalytic domain of the MMP, as well as the catalytic domain of the MMP alone, and truncated forms of the catalytic domain of the MMP that retain at least some catalytic activity.

It should be appreciated that it has been shown previously (Ye Qi-Zhuang, et al., supra., 1996) that inhibitor activity against a catalytic domain of an MMP is predictive of the inhibitor activity against the respective full-length enzyme.

The phrases "pharmaceutical preparation" and "preparation" are synonymous unless otherwise indicated, and include the formulation of the active compound with encapsulating material as a carrier providing a capsule in which the active component, with or without other carriers, is surrounded by a carrier, which is thus in association with it. Similarly, cachets and lozenges are included. Pharmaceutical preparations are fully described below.

The phrase "admixed" or "in admixture" means the ingredients so mixed comprise either a heterogeneous or homogeneous mixture. Preferred is a homogeneous mixture.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention. Some of the compounds may have chiral centers. The invention includes all racemates, pure enantiomers, and all geometric and positional isomers.

The compounds of Formula I, II, III, or IV are capable of further forming both pharmaceutically acceptable formulations comprising salts, including but not limited to acid addition and/or base salts, solvates and N-oxides of a compound of Formula I, II, III, or IV. This invention also provides pharmaceutical formulations comprising a compound of Formula I, II, III, or IV, together with a pharmaceutically acceptable carrier, diluent, or excipient therefor. All of these forms can be used in the method of the present invention.

Pharmaceutically acceptable acid addition salts of the compounds of Formula I, II, III, or IV include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science*, 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge, et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The compounds of the present invention can be formulated and administered in a wide variety of oral and parenteral dosage forms, including transdermal and rectal administration. All that is required is that an MMP inhibitor be administered to a mammal suffering from a disease in an effective amount, which is that amount required to cause an improvement in the disease and/or the symptoms associated with such disease. It will be recognized to those skilled in the art that the following dosage forms may comprise as the active component, either a compound of Formula I, II, III, or IV or a corresponding pharmaceutically acceptable salt or solvate of a compound of Formula I, II III, or IV.

The invention compounds are prepared by methods well known to those skilled in the art of organic chemistry. The compounds of Formula I are prepared utilizing commercially available starting materials, or reactants that are readily prepared by standard organic synthetic techniques. A typical synthesis of the invention compounds of Formula I is shown in Scheme 1 below, which illustrates the coupling of a biphenylsulfonyl halide to a suitably substituted thiomorpholine.

The first step in Scheme 1 comprises reacting a suitably substituted biphenylsulfonyl chloride (compound 1) with a thiomorpholine carboxylic acid ester (compound 2). The compounds are combined in approximately equimolar quantities in a mutual solvent such as pyridine or dioxane, and are stirred at a reduced temperature of about −5° C. to about 10° C. The reaction is generally substantially complete within about 2 to about 10 hours. The product, a biphenylsulfonyl substituted thiomorpholine carboxylic acid ester (3), is isolated by diluting the reaction mixture with aqueous acid and extracting the product into an organic solvent such as ethyl acetate, chloroform, or dichloromethane. The product ester can be further purified, if desired, by standard methods such as chromatography, crystallization, distillation, and the like.

The biphenylsulfonyl-thiomorpholine carboxylic acid esters are readily hydrolyzed to the carboxylic acids (4) of Formula I by standard methods, for example by reaction with an acid such as trifluoroacetic acid in a solvent such as anisole or dimethylsulfoxide.

Scheme 1 further illustrates the synthesis of hydroxamic acids (5) of Formula I (X=NHOH) by simply reacting the biphenyl sulfonyl-thiomorpholine carboxylic acid (4) with oxalyl chloride to give the corresponding acid chloride, and then reacting the acid chloride with hydroxylamine. The reaction generally is carried out in a mutual solvent such as tetrahydrofuran or dioxane, and is substantially complete within about 2 to 20 hours when carried out at a temperature of about 0° C. to about 25° C. The product hydroxamic acid (5) is readily isolated by extraction into an organic solvent such as diethyl ether or ethyl acetate, and concentration to dryness. The hydroxamic acids can be purified, if desired, by standard methods such as crystallization or chromatography over solid supports such as silica gel.

Scheme 1a illustrates the synthesis of sulfoxides and sulfones of Formula I (Y=SO or $SO_2$). The biphenylsulfonyl-thiomorpholine carboxylic acid esters (3) are reacted with an oxidizing agent such as peracetic acid or m-chloroperbenzoic acid. Reaction of the ester with one equivalent of oxidizing agent provides the invention sulfoxides (Y=SO), and reaction with two equivalents or more effects complete oxidation to the corresponding sulfones (Y=$SO_2$) (6).

As shown in Scheme 1a and discussed above, the carboxylic acid esters (of either a thiomorpholine sulfoxide or sulfone) (e.g., 6) is readily hydrolyzed to the carboxylic acids of Formula I (7), which are potent MMP inhibitors, and which can be readily converted to the invention hydroxamic acids (8).

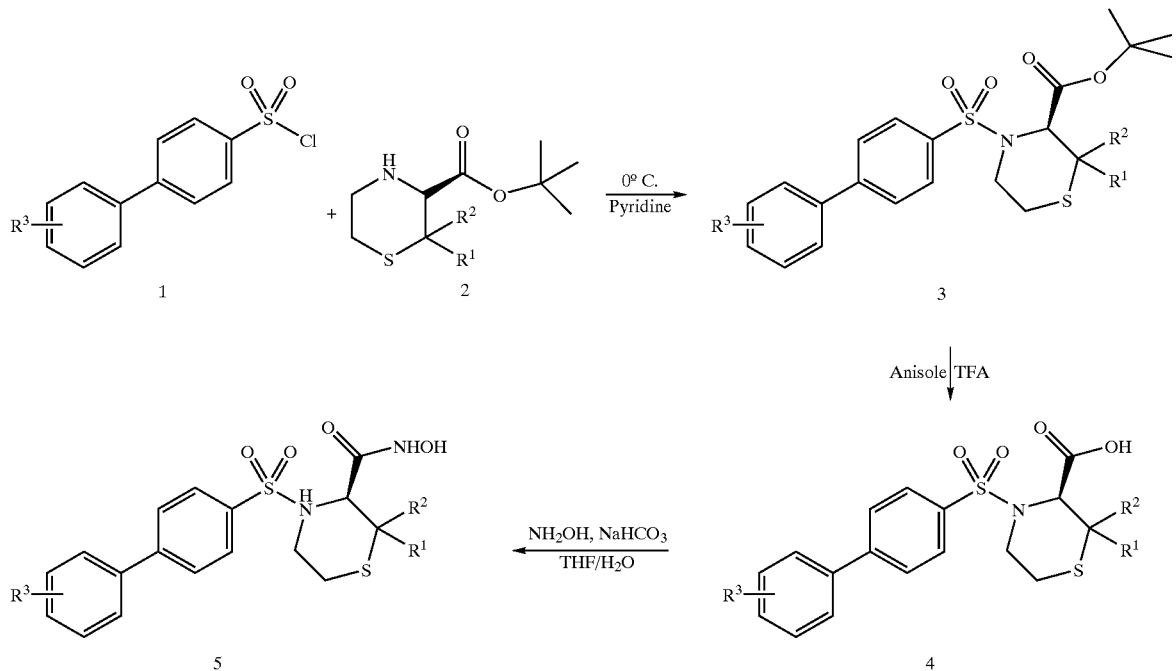

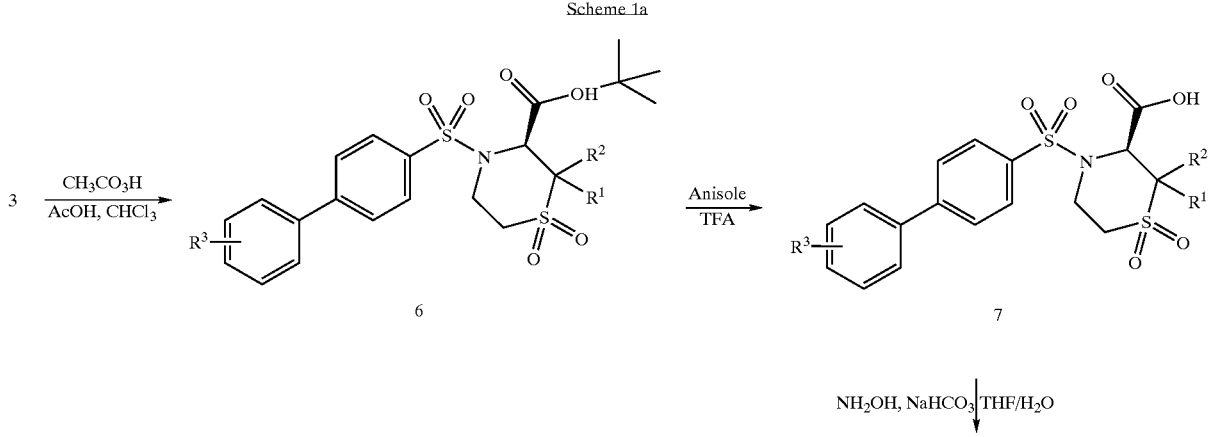

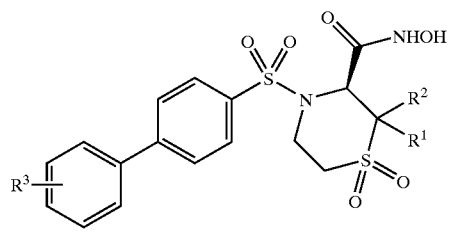

Scheme 2 illustrates an alternative synthesis of the biphenyl invention compounds wherein a thiomorpholine is condensed with a phenylsulfonyl chloride, wherein the phenyl bears a good leaving group "L" as a substituent. Good leaving groups are halogens such as bromo and iodo. A preferred reactant is pipsyl chloride (4-iodobenzenesulfonyl chloride). The condensation is carried out in a manner analogous to that described above for the biphenyl series, is isolated by removing excess solvents and extraction into an organic solvent such as ethyl acetate or diethyl ether. The product can be further purified by chromatography, crystallization or the like. The thiomorpholine carboxylic acid esters (3) are readily hydrolyzed to the free acids (4) by the methods described above, and the carboxylic acids can be converted to the corresponding hydroxamic acids by standard methods.

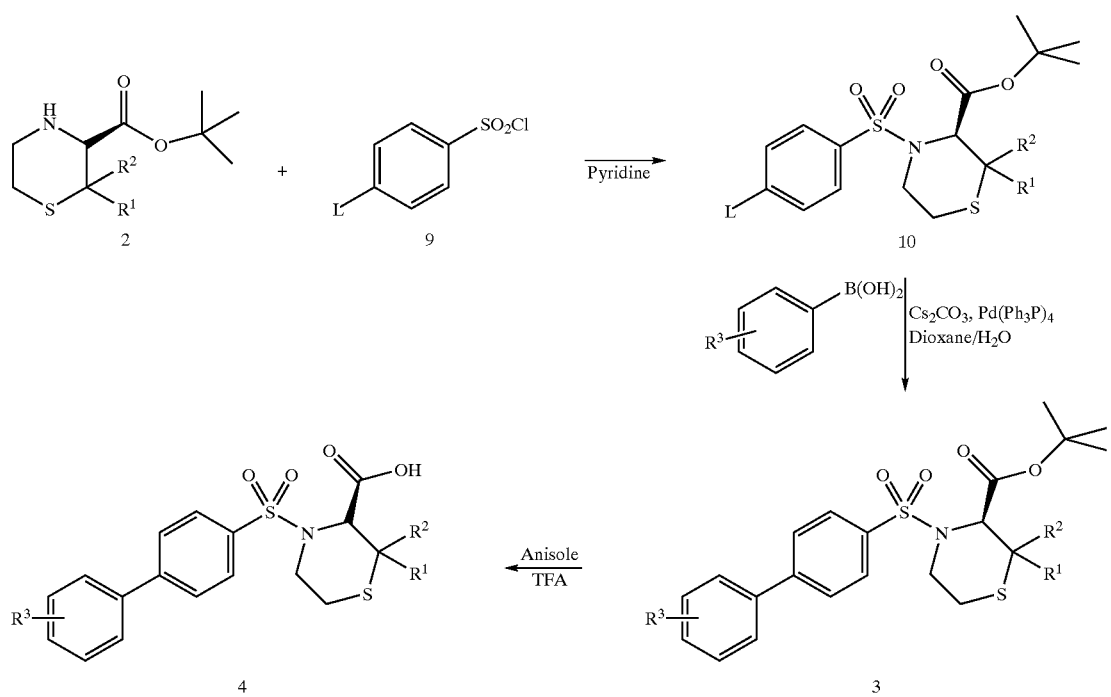

Scheme 2 and the product is an "L" substituted phenylsulfonyl-thiomorpholine carboxylic acid ester (10). The leaving group "L" is readily displaced by reaction with any $R^3$ substituted phenyl boronic acid compound to provide the corresponding $R^3$ substituted biphenylsulfonyl-thiomorpholine carboxylic acid ester (3). The displacement reaction is accomplished by reacting the "L" substituted phenylsulfonyl thiomorpholine with an equimolar quantity, or slight excess, of the benzene boronic acid in a mutual solvent such as dioxane. The reaction is generally carried out at an elevated temperature of about 60° C. to 90° C., and generally is complete within 4 to 12 hours. The product (3)

Scheme 3 illustrates derivatization on the terminal phenyl ring of the biphenylsulfonyl-thiomorpholine carboxylic acids where $R^3$ is a hydroxymethyl group. The hydroxymethyl group readily reacts with methanesulfonyl chloride (MSCl) to provide the corresponding methanesulfonyloxy methyl substituted biphenyl analog. The methanesulfonyloxy methyl substituted biphenyl analog group is a good leaving group (L) and is readily displaced by nucleophiles such as amines ($HNR^5R^6$) to provide the corresponding aminoalkyl substituted biphenyl invention compound (12). These compounds can be further hydrolyzed to the free acids (13), which can be converted to the hydroxamic acids, all as described above.

Scheme 3

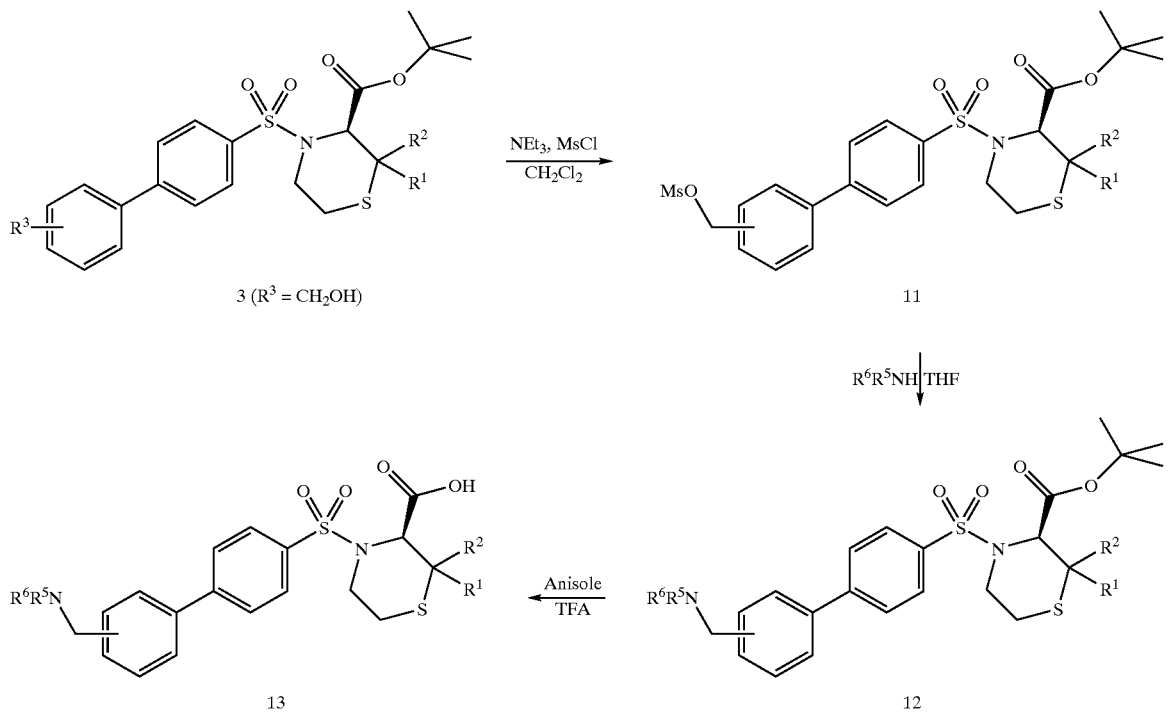

The invention compounds of Formula I are ideally suited to synthesis by general combinatorial methodologies. Schemes 4 and 5 illustrate the use of resin supports to facilitate the synthesis of invention compounds. As shown in Scheme 4, a phenylsulfonyl-thiomorpholine carboxylic acid (14) bearing a good leaving group (L=I) on the phenyl ring is reacted with a hydroxyl amine that is attached to a solid resin (e.g., a polystyrene resin "PS") through the oxygen atom to provide a phenylsulfonyl-thiomorpholine hydroxamic acid (15) bound to a resin support (PS). The leaving group (L=I) is displaced by reaction with a suitably substituted phenyl boronic acid by the general process described above. The biphenyl analog (16) that is produced is next liberated from the resin support (PS) by reaction with an acid such as trifluoroacetic acid to give the corresponding hydroxamic acid of the invention (5).

Scheme 5 illustrates that the biphenylsulfonyl-thiomorpholine hydroxamic acid-resin complex (16) can be further modified to provide the aminoalkyl substituted biphenyl thiomorpholine hydroxamic acids of the invention (19).

Scheme 4

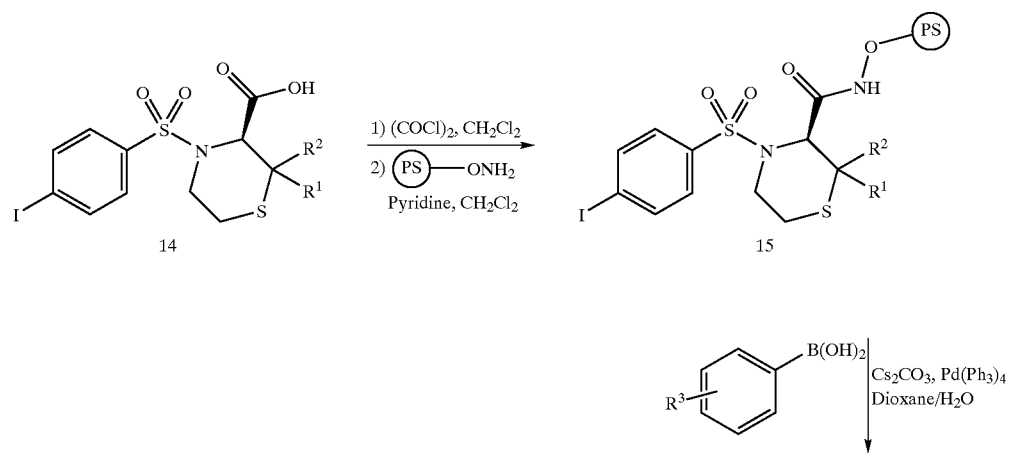

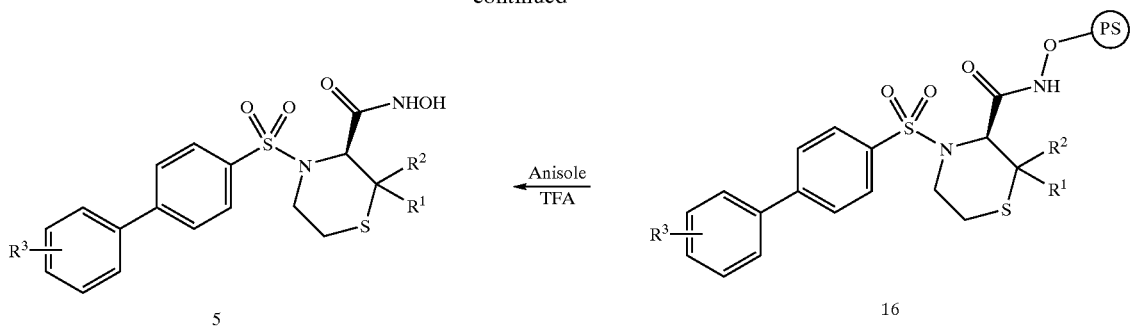

Scheme 5

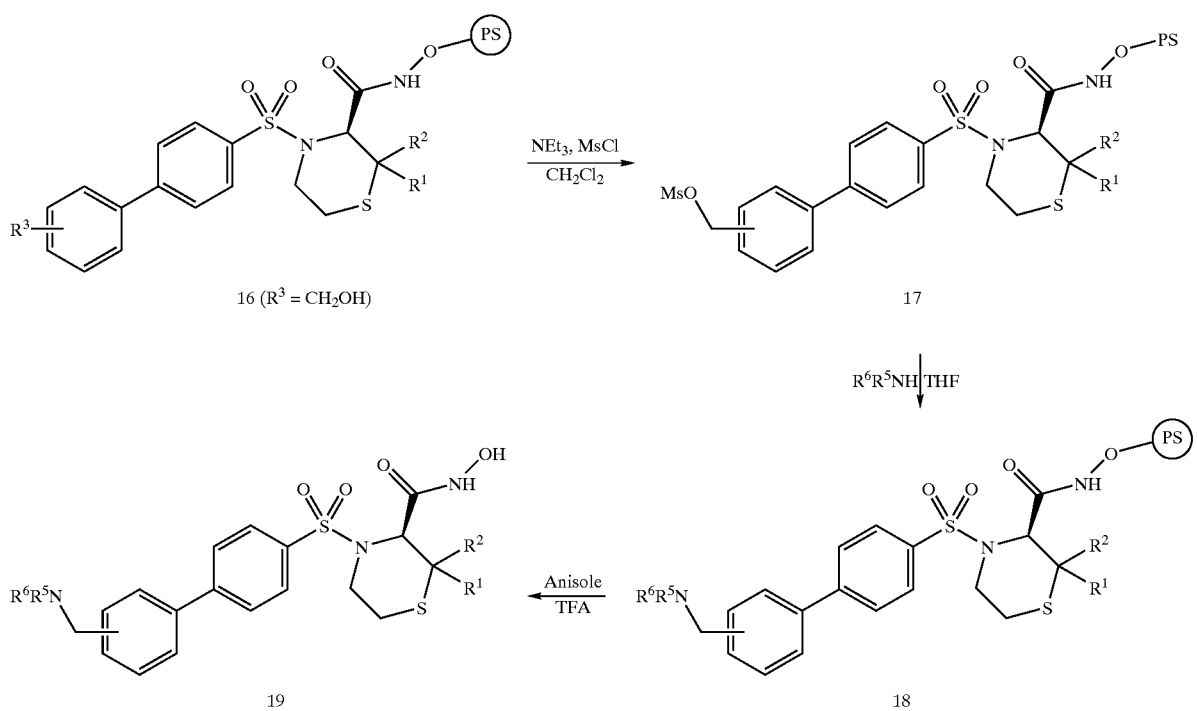

It should be appreciated that compounds of Formula III may be readily prepared by adapting the procedures illustrated in Schemes 2 and 4, wherein the phenylboronic acid intermediates used in the second steps are replaced with thiopheneboronic acid intermediates of formula (A)

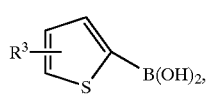

(A)

Wherein $R^3$ is as defined above for Formula III.

It may be desirable to derivatize certain reactive functional groups during chemical reactions in order to avoid unwanted side reactions. Groups such as carboxylic acids, amines and hydroxy groups generally are protected with any of a number of common protecting groups that can be readily removed when desired. The use of protecting groups in organic synthesis is fully described by Greene and Wuts in *Protecting Groups in Organic Synthesis*, (John Wiley & Son Press, $2^{nd}$ edition), which is incorporated herein by reference. Typical amino acid hydroxy protecting groups include acyl groups such as formyl, acetyl, and benzoyl. Typical protecting groups for carboxylic acids include ester-forming groups such as tert-butyl, 2,2,2-trichloroethyl, and benzyl. Other common protecting groups include tert-butoxycarbonyl (BOC) and trimethylsilyl.

The following detailed examples further illustrate the synthesis of typical invention compounds of Formula I and Formula III. The examples are representative only, and are not to be construed as limiting the invention in any respect. All references cited herein are incorporated by reference.

EXAMPLE 1

(S)-4-(4'-Bromo-biphenyl-4-sulfonyl)-2,2-dimethyl-thiomorpholine-3-carboxylic acid (a) To a stirred solution of 3(S)-2,2-dimethyl-3-thiomorpholine carboxylic acid, 1,1-dimethylethyl ester hydrochloride (11.5 g, 0.049 mol) in pyridine (100 mL), cooled to 0° C., was added in portions over 15 minutes 4'-bromo-4-biphenylsulfonyl chloride (15 g, 0.045 mol). The solution was stirred at 0° C. for 4 hours, then concentrated in vacuo. The crude product was partitioned between aq. HCl (1 M) and ethyl acetate, the layers separated, and the organic phase was washed with aq. HCl (1 M), dried (MgSO$_4$), and concentrated. The resulting orange liquid was diluted with chloroform and passed through a pad of silica gel. Fractions containing the product were combined and concentrated to give a colorless liquid. Trituration with petroleum ether/diethyl ether (9:1) yielded a white solid (13.5 g, 57%). $^1$HNMR (CDCl$_3$) δ 7.8 (d, 2H), 7.6 (m, 4H), 7.4 (d, 2H), 4.3 (s, 1H), 4.1 (m, 1H), 3.9 (m, 1H), 3.2 (m, 1H), 2.4 (m, 1H), 1.6 (s, 3H0, 1.3 (s, 3H), 1.2 (s, 9H) ppm.

(b) The ester obtained in (a) (13.5 g, 0.026 mol) was added in portions to a solution of anisole (2.8 g, 0.026 mol) in trifluoroacetic acid (100 mL). The solution was stirred at room temperature for 3 hours, and then poured over ice. The resulting precipitate was collected by filtration and oven-dried (40° C.). The crude product was triturated with petroleum ether/diethyl ether (4: 1) to give the carboxylic acid as a white solid. Yield: 11 g (90%); mp 178–180° C.; $^1$HNMR (DMSO-d$_6$) δ 12.8 (bs, 1H), 7.9 (d, 2H), 7.8 (d, 2H), 7.7 (s, 4H), 4.3 (s, 1H), 3.9 (m, 1H), 3.7 (m, 1H), 2.9 (m, 1H), 2.5 (m, 1H), 1.4 (s, 3H), 1.2 (s, 3H) ppm.

EXAMPLE 2

(S)-4-(4'-Bromo-biphenyl-4-sulfonyl)-2,2-dimethyl-thiomorpholine-3-carboxylic acid hydroxyamide The carboxylic acid obtained in Example 1 (12.2 g, 0.026 mol) was diluted with dichloromethane (150 mL) and oxalyl chloride (16.5 g, 0.13 mol). N,N-Dimethylformamide was added as a catalyst. The solution was stirred at room temperature for 14 hours, at which time the solvent was concentrated in vacuo. The crude acid chloride was triturated with hexane and collected by filtration. The solid was diluted with tetrahydrofuran (75 mL) and added dropwise to a mixture of hydroxylamine hydrochloride (9 g, 0.13 mol) and sodium bicarbonate (16.4 g, 0.19 mol) in tetrahydrofuran (150 mL)/water (75 mL) cooled to 0° C. The reaction mixture gradually warmed to room temperature and was stirred for 14 hours. Ethyl acetate and aq. HCl (1M) were added, the layers were separated, and the organic portion was washed with brine, dried (MgSO$_4$), and concentrated. The resulting viscous liquid yielded a white solid (11.4 g, 90%) upon treatment with cold diethyl ether/petroleum ether (4:1), mp 190–192° C.; $^1$HNMR (DMSO-d$_6$) δ 10.7 (s, 1H), 8.9 (s, 1H), 4.1 (s, 1H), 4.0 (m, 1H), 3.8 (m, 1H), 2.9 (m, 1H), 2.5 (m, 1H), 1.4, (s, 3H), 1.1 (s, 3H) ppm.

EXAMPLE 3

(S)-4-(4'-Bromo-biphenyl-4-sulfonyl)-2,2-dimethyl-1,1-dioxo-thiomorpholine-3-carboxylic acid (a) The ester obtained in (a) of Example 1 (1 g, 1.9 mmol) was diluted with chloroform, cooled to 0° C., followed by the dropwise addition of peracetic acid (32% in acetic acid; 1 g, 4.2 mmol). The solution was allowed to warm to room temperature and was stirred for 3 hours. The product was washed with saturated sodium bisulfite, brine, and dried over Na$_2$SO$_4$. The solvent was concentrated in vacuo, and the resulting solid was suspended in diethyl ether and collected by filtration. Yield: 0.82 g (82%); $^1$HNMR (CDCl$_3$) δ 7.8 (d, 2H), 7.7 (d, 2H), 7.6 (d, 2H), 7.4 (d, 2H), 4.6 (s, 1H), 4.44.2 (m, 2H), 3.5 (m, 1H), 2.9 (m, 1H), 1.8 (s, 3H), 1.6 (S, 3H), 1.3 (s, 9H) ppm.

(a) The sulfone obtained in (a) (0.81 g, 1.4 mmol) was added in portions to a solution of anisole (0.16 g, 1.4 mmol) in trifluoroacetic acid (15 mL). The solution was stirred for 3 hours at room temperature, then poured over ice. The resulting precipitate was collected by filtration and oven-dried (40° C.). The solid was triturated with diethyl ether and collected by filtration. Yield: 0.5 g, (68%); mp 262–263° C.; $^1$HNMR (DMSO-d$_6$) δ 7.9 (m, 4H), 7.7 (s, 4H), 4.7 (s, 1H), 4.2 (m, 2H), 3.5 (m, 1H), 3.2 (m, 2H), 1.5 (d, 6H) ppm.

EXAMPLE 4

(S)-4-(4'-Bromo-biphenyl-4-sulfonyl)-2,2-dimethyl-1,1-dioxo-thiomorpholine-3-carboxylic acid hydroxyamide Utilizing the experimental conditions described in Example 2, the title compound was obtained as a white solid. mp 190–191° C.; $^1$HNMR (DMSO-d$_6$) δ 10.6 (s, 1H), 9.0 (bs, 1H), 7.9 (d, 2H), 7.8 (d, 2H) 7.7 (s, 4H), 4.7 (m, 1H), 4.3 (s, 1H), 4.1 (d, 1H), 3.4 (m, 1H), 3.2 (d, 1H), 1.4 (s, 3H), 1.3 (s, 3H) ppm.

General procedures for preparation of substituted biphenyl derivatives utilizing combinatorial synthesis (Schemes 2–5).

EXAMPLE 5

(S)-4-(4'-Hydroxymethyl-biphenyl-4-sulfonyl)-2,2-dimethyl-thiomorpholine-3-carboxylic acid (a) To a solution of 3(S)-2,2-dimethyl-3-thiomorpholine carboxylic acid,1,1-dimethylethylester (10.41 g, 0.045 mol) in pyridine (300 mL), was added pipsyl chloride (13.31 g, 0.044 mol) in one portion. Solution was stirred at room temperature overnight then concentrated in vacuo. Resulting solid was taken up in CH$_2$Cl$_2$ (300 mL) and washed with citric acid (10%, 2×300 mL). Organic layer was isolated, washed with brine (2×300 mL) then concentrated in vacuo to give (S)-4-(iodo-phenyl-1-sulfonyl)-2,2-dimethyl-thiomorpholine-3-carboxylic acid as a yellow solid (20.56 g, 94% yield); $^1$HNMR (CDCl$_3$) δ 7.8 (d, 2H), 7.4 (d, 2H), 4.3 (s, 1H), 4.0 (td, 1H), 3.9 (dt, 1H), 3.1 (dt, 1H), 2.5 (td, 1H), 1.6 (s, 3H), 1.4 (s, 3H), 1.3 (s, 9H) ppm.

(b) To solution of ester from (a) (1 mL of a 0.3 M solution in dioxane, 0.3 mmol) in a 2-dram vial equipped with a stir bar was added a solution of 4-hydroxymethyl-benzene boronic acid (2 mL of a 0.2 M solution in dioxane/2.5 M aq Na$_2$CO$_3$ [3 M equivalents relative to the boronic acid], 0.4 mmol). In a dry, oxygen free environment, approximately 40 mg of Pd(PPh$_3$)$_4$ was added. Vial was capped and heated at 75° C. while being stirred overnight. Solution was cooled to room temperature, concentrated in vacuo, and diluted with EtOAc (2 mL). Crude product was filtered and the filtrate collected, and concentrated in vacuo. The product was characterized by MS.

(c) Ester obtained in (b) was added to a solution of anisole in trifluoroacetic acid (1 mL of a 0.3 M solution). Removal of TFA by concentration gave the crude compound. Purification by column chromatography and characterization by LC-MS afforded the title compound as a white solid. $^1$HNMR (DMSO-d$_6$) δ 12.8 (s,1 H), 7.8 (d, 2H), 7.7 (d, 2H), 7.6 (d, 2H), 7.4 (d, 2H), 5.2 (t, 1H), 4.5 (d, 1H), 4.3 (s, 1H), 3.9 (m, 1H), 3.6 (m, 1H), 2.9 (m, 1H), 2.5 (m, 1H), 1.4 (s, 3H), 1.2 (s, 3H) ppm.

Examples 6–11

Replacement of 4-hydroxybenzeneboronic acid in part (b) of Example 5 with appropriately substituted benzeneboronic acids yield the following derivatives:

EXAMPLE 6

(S)-4-(2'-Carboxy-biphenyl-4-sulfonyl)-2,2-dimethyl-thiomorpholine-3-carboxylic acid

EXAMPLE 7

(S)-4-(4'-Methanesulfonyl-biphenyl-4-sulfonyl)-2,2-dimethyl-thiomorpholine-3-carboxylic acid

EXAMPLE 8

(S)-4-(4'-Formyl-biphenyl-4-sulfonyl)-2,2-dimethyl-thiomorpholine-3-carboxylic acid

EXAMPLE 9

(S)-4-(3'-Formyl-biphenyl-4-sulfonyl)-2,2-dimethyl-thiomorpholine-3-carboxylic acid

EXAMPLE 10

(S)-4-(4'-Dimethylamino-biphenyl-4-sulfonyl)-2,2-dimethyl-thiomorpholine-3-carboxylic acid

EXAMPLE 11

(S)-4-(2'-Bromo-biphenyl-4-sulfonyl)-2,2-dimethyl-thiomorpholine-3-carboxylic acid General method to synthesize aminomethyl-substituted biphenyl derivatives.

EXAMPLE 12

(S)-4-{4'-[(2-Hydroxy-ethylamino)-methyl]-biphenyl-4-sulfonyl}-2,2-dimethyl-thiomorpholine-3-carboxylic acid (a) To a solution of hydroxymethylbiphenyl ester from Example 5b (0.5 mL of a 0.4 M solution in $CH_2Cl_2$) in a 2-dram vial cooled to ~0° C. was added a solution of mesyl chloride (0.5 mL of a 0.4 M solution in $CH_2Cl_2$) in a dry oxygen free environment. Solution was stirred for 5 minutes then a portion of $Et_3N$ (0.4 mmol) was added. This solution was stirred at ~0° C. for 30 minutes. Solution was concentrated and used without further characterization.

(b) Crude product from (a) was diluted up in anhydrous THF (1 mL) in a dry environment and then cooled to ~0° C. To this solution was added ethanolamine (1 mL of a 0.2 M solution in dry THF). This was allowed to warm to room temperature while stirring overnight. Concentration in vacuo, followed by hydrolysis of the ester as described in part (c) of Example 5 gave the title compound.

Replacement of ethanolamine in Example 12b with a variety of substituted amines yields the compounds of Examples 13 to 17.

EXAMPLE 13

(S)-4-{4'-[(Diisopropylamino)-methyl]-biphenyl-4-sulfonyl}-2,2-dimethyl-thiomorpholine-3-carboxylic acid

EXAMPLE 14

(S)-4-[4'-(Isobutylamino-methyl)-biphenyl-4-sulfonyl]-2,2-dimethyl-thiomorpholine-3-carboxylic acid

EXAMPLE 15

(S)-2,2-Dimethyl-4-(4'-pyrrolidin-1-ylmethyl-biphenyl-4-sulfonyl)-thiomorpholine-3-carboxylic acid

EXAMPLE 16

(S)-4-(4'-Cyclohexylaminomethyl-biphenyl-4-sulfonyl)-2,2-dimethyl-thiomorpholine-3-carboxylic acid

EXAMPLE 17

(S)-2,2-Dimethyl-4-(4'-thiomorpholin-4-ylmethyl-biphenyl-4-sulfonyl)-thiomorpholine-3-carboxylic acid Example 18 describes the general procedure for preparing (S)-(substituted-biphenyl-4-sulfonyl)-2,2-dimethyl-thiomorpholine-3-carboxylic acid hydroxamide derivatives via solid phase synthesis.

EXAMPLE 18

(S)-4-(4'-Hydroxymethyl-biphenyl-4-sulfonyl)-2,2-dimethyl-thiomorpholine-3-carboxylic acid hydroxyamide (a) To a solution of acid (compound 14, Scheme 4) (1.76 g, 0.4 M in $CH_2Cl_2$/DMF 4:1) was added 1,3-diisopropyl-carbodiimide (0.51 g, 0.004 mol), and N,N-dimethylaminopyridine (0.048 g 0.0004 mol) followed by Wang-O-hydroxylamine resin (Salvino et al., *J. Org. Chem.* 1999;64:1823–1830) prepared in house (1.0 g of 1 mmol/g loaded resin). Solution shaken at room temperature over 2 days. Resin was washed with alternating $CH_2Cl_2$ (10 mL) then MeOH (10 mL) four times. Resin dried in vacuo. Weight gain, IR, and iodine analysis point to theoretical loading of O-Wang resin product.

(b) Resin (0.1 g, 0.1 mmol) from part (a) was portioned out to a 2-dram vial equipped with a stir bar. A solution of 4-hydroxymethyl-benzene boronic acid (2 mL of a 0.2 M solution in dioxane/2.5 M aq. $Na_2CO_3$ [3 molar equivalents relative to the boronic acid], 0.4 mmol) was added. In a dry, oxygen free environment, approximately 40 mg of $Pd(PPh_3)_4$ was added. Vial was capped and heated at 75° C. while being stirred overnight. Solution was cooled to room temperature, filtered, and the resin washed with alternating portions of $CH_2Cl_2$ (2 mL) and MeOH (2 mL) four times.

(c) Solution of $CH_2Cl_2$/TFA (50%) was added to resin from (c). Mixture stirred for 3 hours at room temperature. Resin solution was filtered and the resin washed with two portions of $CH_2Cl_2$ (1 mL) each. Filtrates combined and concentrated in vacuo. Purification by column followed by identification by LC-MS gave the title compound.

EXAMPLES 19–20

Utilizing the general procedures from Example 18, the compounds of Examples 19 and 20 may be prepared:

EXAMPLE 19

(S)-4-(3'-Amino-biphenyl-4-sulfonyl)-2,2-dimethyl-thiomorpholine-3-carboxylic acid hydroxyamide

EXAMPLE 20

(S)-4-(4'-Dimethylamino-biphenyl-4-sulfonyl)-2,2-dimethyl-thiomorpholine-3-carboxylic acid hydroxyamide

EXAMPLE 21

(S)-4-(3'-Bromo-biphenyl-4-sulfonyl)-2,2-dimethyl-thiomorpholine-3-carboxylic acid hydroxyamide Solid phase synthesis of aminomethyl substituted biphenyl hydroxyamide derivatives.

(a) (S)-4-(4-Iodophenyl-1-sulfonyl)-2,2-dimethyl-thiomorpholine-3-carboxylic acid hydroxamide-O-Wang resin (15, Scheme 4) (5.0 g at 1 mmol/g loading, 5 mmol) was swelled in dioxane (40 mL). To this was added 4-hydroxymethylbenzene boronic acid (30 mL of a 0.5 M solution in dioxane/2.5 M aq. $Na_2CO_3$ [3 M equivalents relative to the boronic acid], 15 mmol). In a dry, oxygen free environment $Pd(PPh_3)_4$ (200 mg) was added, and the mixture was stirred while at 75° C. for 48 hours. Filtration and subsequent resin washing three times with alternating $CH_2Cl_2$ (20 mL) followed by THF (20 mL) gave the (S)-4-(4'-hydroxymethyl-biphenyl-4-sulfonyl)-2,2-dimethyl-thiomorpholine-3-carboxylic acid hydroxamide-O-Wang resin.

(b) To resin from (a) (0.140 g, 1 mmol) in $CH_2Cl_2$ (2 mL) cooled to ~0° C. was added a solution of mesyl chloride (0.5 mL of a 0.4 M solution in $CH_2Cl_2$) in a dry oxygen free environment. Solution was stirred for 5 minutes then a portion of $Et_3N$ (0.4 mmol) was added. This solution was stirred at ~0° C. for 30 minutes. Mixture was filtered and washed with $CH_2Cl_2$ (5 mL) three times and filtrates discarded. Resin was immediately used in (c).

(c) Resin from (b) was diluted up in dry THF/$CH_2Cl_2$ (1 mL of 50% solution) in a dry environment and then cooled to ~0° C. To this solution was added an amine (2 mL of a 0.2 M solution in dry THF). This was allowed to warm to room temperature while stirring overnight. Filtration of resin mixture, then three sets of washings with $CH_2Cl_2$ (5 mL) followed by THF (5 mL) gave O-Wang title product.

Utilizing the experimental conditions of Example 21 and of step (c) of Example 18, the compounds of Examples 22–25 may be obtained.

EXAMPLE 22

(S)-2,2-Dimethyl-4-(4'-piperidin-1-ylmethyl-biphenyl-4-sulfonyl)-thiomorpholine-3-carboxylic acid hydroxyamide

EXAMPLE 23

(S)-4-{4'-[(Benzyl-isopropyl-amino)-methyl]-biphenyl-4-sulfonyl}-2,2-dimethyl-thiomorpholine-3-carboxylic acid hydroxyamide

EXAMPLE 24

(S)-2,2-Dimethyl-4-[4'-(4-methyl-piperazin-1-ylmethyl)-biphenyl-4-sulfonyl]-thiomorpholine-3-carboxylic acid hydroxyamide

EXAMPLE 25

(S)-2,2-Dimethyl-4-(4'-piperidin-1-ylmethyl-biphenyl-4-sulfonyl)-thiomorpholine-3-carboxylic acid hydroxyamide General Method for the Preparation of the Compounds of Examples 26 to 65

Step (a): HO-resin esterified with (S)-4-(iodo-phenyl-1-sulfonyl)-2,2-dimethyl-thiomorpholine-3-carboxylic acid In a manner similar to the procedure of Example 18, Step (a), HO-resin was coupled with (S)-4-(iodo-phenyl-1-sulfonyl)-2,2-dimethyl-thiomorpholine-3-carboxylic acid to give (S)-4-(iodo-phenyl-1-sulfonyl)-2,2-dimethyl-thiomorpholine-3-carboxylic acid, ester with HO-resin. Theoretical loading of the resin was determined by weight gain, infrared spectroscopy ("IR"), and iodine elemental analysis.

Step (b): Preparation of resin-attached carboxylic ester corresponding to the title carboxylic acid To a 2-dram vial was added an amount of the resin from Step (a) that contained 0.15 mmoles of the compound of Example 5, Step (a), followed by 3 mL (4 mol eq.) of a 0.2 M solution of the appropriate boronic acid in dioxane and 0.240 mL of a 2.5 M solution of potassium carbonate in water. To the mixture was added about 30 mg of tetrakis (triphenylphosphine) palladium (0), and the vial was capped and heated at 75° C. with stirring for 4 hours. The reaction mixture and resin was transferred to a Bohdan reaction tube in a Bohdan Miniblock, and the solvent was drained to waste. The resin was washed with N,N-dimethylformamide (4×1.25 mL, draining between each wash), followed by a sequential wash of 4×[$CH_2Cl_2$ (1.25 mL), then methanol (1.25 mL), draining between each wash]. The resin was washed with $CH_2Cl_2$ (1.25 mL) then dried to give resin attached carboxylic ester of the title compound;

Step (c): Preparation of the title carboxylic acid

To each of the reaction tubes, was added 2 mL of 50% trifluoroacetic acid ("TFA") in $CH_2Cl_2$, and the reaction was shaken overnight. The cleavage solution was filtered off into a tube in a Bohdan collection block, and the resin filtercake was rinsed with $CH_2Cl_2$ (2×0.50 mL). The filtrate and washing was analyzed by mass spectrometry, and the solution was concentrated in a Genevac, and the residue purified by high performance liquid chromatography ("HPLC") to give the title carboxylic acid.

The compounds of Examples 26 to 65 were prepared according to the above-described general method.

EXAMPLE 26

(S)-4-(4'-Bromo-biphenyl-4-sulfonyl)-2,2-dimethyl-thiomorpholine-3-carboxylic acid

MS APCI: 436.5

LC purity: 100%

EXAMPLE 27

(S)-2,2-Dimethyl-4-(3'-nitro-biphenyl-4-sulfonyl)-thiomorpholine-3-carboxylic acid

MS APCI: 436.5

LC purity: 100%

EXAMPLE 28

(S)-2,2-Dimethyl-4-(4-naphthalen-1-yl-benzenesulfonyl)-thiomorpholine-3-carboxylic acid

MS APCI: 441.6

LC purity: 84.07%

EXAMPLE 29

(S)-4-(4'-Chloro-biphenyl-4-sulfonyl)-2,2-dimethyl-thiomorpholine-3-carboxylic acid

MS APCI: 425.9

LC purity: 73.52%

EXAMPLE 30

(S)-4-(4'-Formyl-biphenyl-4-sulfonyl)-2,2-dimethyl-thiomorpholine-3-carboxylic acid MS APCI: 419.5
LC purity: 87.03%

EXAMPLE 31

(S)-2,2-Dimethyl-4-(3'-methyl-biphenyl-4-sulfonyl)-thiomorpholine-3-carboxylic acid MS APCI: 405.5
LC purity: 82.12%

EXAMPLE 32

(S)-4-(4'-Fluoro-biphenyl-4-sulfonyl)-2,2-dimethyl-thiomorpholine-3-carboxylic acid

EXAMPLE 33

(S)-4-(4-1,3-Benzodioxol-5-yl-benzenesulfonyl)-2,2-dimethyl-thiomorpholine-3-carboxylic acid MS APCI: 435.5
LC purity: 100%

EXAMPLE 34

(S)-4-(3'-Chloro-biphenyl-4-sulfonyl)-2,2-dimethyl-thiomorpholine-3-carboxylic acid MS APCI: 425.9
LC purity: 97.14%

EXAMPLE 35

(S)-4-(3'-Formyl-biphenyl-4-sulfonyl)-2,2-dimethyl-thiomorpholine-3-carboxylic acid MS APCI: 419.5
LC purity: 79.7%

EXAMPLE 36

(S)-2,2-Dimethyl-4-(4-naphthalen-2-yl-benzenesulfonyl)-thiomorpholine-3-carboxylic acid MS APCI: 441.6
LC purity: 100%

EXAMPLE 37

(S)-2,2-Dimethyl-4-(4-methylsulfanyl-biphenyl-4-sulfonyl)-thiomorpholine-3-carboxylic acid MS APCI: 437.6
LC purity: 100%

EXAMPLE 38

(S)-2,2-Dimethyl-4-([1,1';4',1"]terphenyl-4-sulfonyl)-thiomorpholine-3-carboxylic acid MS APCI: 467.6
LC purity: 100%

EXAMPLE 39

(S)-4-(2',4'-Difluoro-biphenyl-4-sulfonyl)-dimethyl-thiomorpholine-3-carboxylic acid MS APCI: 427.5
LC purity: 100%

EXAMPLE 40

(S)-2,2-Dimethyl-4-(4'-phenoxy-biphenyl-4-sulfonyl)-thiomorpholine-3-carboxylic acid MS APCI: 483.6
LC purity: 100%

EXAMPLE 41

(S)-4-(3',4'-Difluoro-biphenyl-4-sulfonyl)-2,2-dimethyl-thiomorpholine-3-carboxylic acid MS APCI: 427.5
LC purity: 100%

EXAMPLE 42

(S)-4-(3'-Chloro-4'-fluoro-biphenyl-4-sulfonyl)-2,2-dimethyl-thiomorpholine-3-carboxylic acid MS APCI: 443.9
LC purity: 100%

EXAMPLE 43

(S)-4-(4'-Ethoxy-biphenyl-4-sulfonyl)-2,2-dimethyl-thiomorpholine-3-carboxylic acid MS APCI: 435.6
LC purity: 100%

EXAMPLE 44

(S)-4-(4'-Isopropyl-biphenyl-4-sulfonyl)-2,2-dimethyl-thiomorpholine-3-carboxylic acid MS APCI: 433.6
LC purity: 100%

EXAMPLE 45

(S)-2,2-Dimethyl-4-(4'-trifluoromethoxy-biphenyl-4-sulfonyl)-thiomorpholine-3-carboxylic acid MS APCI: 475.5
LC purity: 100%

EXAMPLE 46

(S)-4-(4'-Hydroxymethyl-biphenyl-4-sulfonyl)-2,2-dimethyl-thiomorpholine-3-carboxylic acid

EXAMPLE 47

(S)-4-(4'-Ethyl-biphenyl-4-sulfonyl)-2,2-dimethyl-thiomorpholine-3-carboxylic acid MS APCI: 419.5
LC purity: 100%

EXAMPLE 48

(S)-4-(3'-Formyl-4'-methoxy-biphenyl-4-sulfonyl)-2,2-dimethyl-thiomorpholine-3-carboxylic acid MS APCI: 449.5
LC purity: 91.05%

EXAMPLE 49

(S)-4-(4'-tert-Butyl-biphenyl-4-sulfonyl)-2,2-dimethyl-thiomorpholine-3-carboxylic acid MS APCI: 447.6
LC purity: 100%

EXAMPLE 50

(S)-4-[4-(5-Chloro-thiophen-2-yl)-benzenesulfonyl]-2,2-dimethyl-thiomorpholine-3-carboxylic acid MS APCI: 431.9
LC purity: 100%

EXAMPLE 51

(S)-4-(4'-Fluoro-3'-methyl-biphenyl-4-sulfonyl)-2,2-dimethyl-thiomorpholine-3-carboxylic acid MS APCI: 423.5
LC purity: 100%

EXAMPLE 52

(S)-2,2-Dimethyl-4-[4-(5-methyl-thiophen-2-yl)-benzenesulfonyl]-thiomorpholine-3-carboxylic acid MS APCI: 411.6
LC purity: 100%

EXAMPLE 53

(S)-4-(2'-Fluoro-[1,1';4',1"]terphenyl-4"-sulfonyl)-2,2-dimethyl-thiomorpholine-3-carboxylic acid MS APCI: 485.6
LC purity: 100%

EXAMPLE 54

(S)-4-4'-Dimethylamino-biphenyl-4-sulfonyl)-2,2-dimethyl-thiomorpholine-3-carboxylic acid MS APCI: 434.6
LC purity: 80.93%

EXAMPLE 55

(S)-2,2-Dimethyl-4-(3',4',5'-trimethoxy-biphenyl-4-sulfonyl)-thiomorpholine-3-carboxylic acid MS APCI: 481.6
LC purity: 94.85%

EXAMPLE 56

(S)-4-(2',4'-Dichloro-biphenyl-4-sulfonyl)-2,2-dimethyl-thiomorpholine-3-carboxylic acid MS APCI: 460.4
LC purity: 100%

EXAMPLE 57

(S)-2,2-Dimethyl-4-(4'-trifluoromethyl-biphenyl-4-sulfonyl)-thiomorpholine-3-carboxylic acid MS APCI: 459.5
LC purity: 100%

EXAMPLE 58

(S)-4-(3'-Fluoro-biphenyl-4-sulfonyl)-2,2-dimethyl-thiomorpholine-3-carboxylic acid MS APCI: 409.5
LC purity: 100%

EXAMPLE 59

(S)-2,2-Dimethyl-4-(3'-trifluoromethoxy-biphenyl-4-sulfonyl)-thiomorpholine-3-carboxylic acid MS APCI: 475.5
LC purity: 100%

EXAMPLE 60

(S)-4-(2',6'-Dimethoxy-biphenyl-4-sulfonyl)-2,2-dimethyl-thiomorpholine-3-carboxylic acid MS APCI: 451.6
LC purity: 92.12%

EXAMPLE 61

(S)-4-(3'-Acetyl-biphenyl-4-sulfonyl)-2,2-dimethyl-thiomorpholine-3-carboxylic acid MS APCI: 433.5
LC purity: 100%

EXAMPLE 62

(S)-4-(3'-Cyano-biphenyl-4-sulfonyl)-2,2-dimethyl-thiomorpholine-3-carboxylic acid MS APCI: 416.5
LC purity: 94.49%

EXAMPLE 63

(S)-4-(2'-Formyl-biphenyl-4-sulfonyl)-2,2-dimethyl-thiomorpholine-3-carboxylic acid MS APCI: 419.5
LC purity: 100%

EXAMPLE 64

(S)-4-(2'-Fluoro-biphenyl-4-sulfonyl)-2,2-dimethyl-thiomorpholine-3-carboxylic acid MS APCI: 409.5
LC purity: 100%

EXAMPLE 65

(S)-4-(3'-Bromo-biphenyl-4-sulfonyl)-2,2-dimethyl-thiomorpholine-3-carboxylic acid MS APCI: 470.4
LC purity: 92.16%

The following additional invention compounds, wherein $R^3$ is a nitrogen containing substituent group, may be prepared by following the general procedure of Example 21:

(S)-4-{4'-[(Butyl-ethyl-amino)-methyl]-biphenyl-4-sulfonyl}-2,2-dimethyl-thiomorpholine-3-carboxylic acid;

(S)-4-[4'-(2-Formyl-pyrrol-1-ylmethyl)-biphenyl-4-sulfonyl]-2,2-dimethyl-thiomorpholine-3-carboxylic acid;

(S)-4-{4'-[(Cyclohexylmethyl-amino)-methyl]-biphenyl-4-sulfonyl}-2,2-dimethyl-thiomorpholine-3-carboxylic acid;

(S)-4-(4'-{[2-(2-Fluoro-phenyl)-ethylamino]-methyl}-biphenyl-4-sulfonyl)-2,2-dimethyl-thiomorpholine-3-carboxylic acid;

(S)-4-(4'-Cyclohexylaminomethyl-biphenyl-4-sulfonyl)-2,2-dimethyl-thiomorpholine-3-carboxylic acid;
(S)-4-(4'-{[(2-Dimethylamino-ethyl)-methyl-amino]-methyl}-biphenyl-4-sulfonyl)-2,2-dimethyl-thiomorpholine-3-carboxylic acid;
(S)-4-{4'-[(3,3-Diethoxy-propylamino)-methyl]-biphenyl-4-sulfonyl}-2,2-dimethyl-thiomorpholine-3-carboxylic acid;
(S)-4-(4'-Imidazol-1-ylmethyl-biphenyl-4-sulfonyl)-2,2-dimethyl-thiomorpholine-3-carboxylic acid;
(S)-2,2-Dimethyl-4-[4'-(phenethylamino-methyl)-biphenyl-4-sulfonyl]-thiomorpholine-3-carboxylic acid;
(S)-4-(4'-Dipropylaminomethyl-biphenyl-4-sulfonyl)-2,2-dimethyl-thiomorpholine-3-carboxylic acid;
(S)-2,2-Dimethyl-4-[4'-(1,2,4-triazol-4-ylaminomethyl)-biphenyl-4-sulfonyl]-thiomorpholine-3-carboxylic acid;
(S)-2,2-Dimethyl-4-(4'-pyrrolidin-1-ylmethyl-biphenyl-4-sulfonyl)-thiomorpholine-3-carboxylic acid;
(S)-2,2-Dimethyl-4-(4'-{[(tetrahydro-furan-2-ylmethyl)-amino]-methyl}-biphenyl-4-sulfonyl)-thiomorpholine-3-carboxylic acid;
(S)-2,2-Dimethyl-4-[4'-(4-methyl-piperazin-1-ylmethyl)-biphenyl-4-sulfonyl]-thiomorpholine-3-carboxylic acid;
(S)-2,2-Dimethyl-4-(4'-piperidin-1-ylmethyl-biphenyl-4-sulfonyl)-thiomorpholine-3-carboxylic acid;
(S)-2,2-Dimethyl-4-(4'-thiomorpholin-4-ylmethyl-biphenyl-4-sulfonyl)-thiomorpholine-3-carboxylic acid;
(S)-4-(4'-{[Cyclohexyl-(2-hydroxy-ethyl)-amino]-methyl}-biphenyl-4-sulfonyl)-2,2-dimethyl-thiomorpholine-3-carboxylic acid;
(S)-4-{4'-[(1-Ethynyl-cyclohexylamino)-methyl]-biphenyl-4-sulfonyl}-2,2-dimethyl-thiomorpholine-3-carboxylic acid;
(S)-4-{4'-[(2,4-Dimethoxy-benzylamino)-methyl]-biphenyl-4-sulfonyl}-2,2-dimethyl-thiomorpholine-3-carboxylic acid;
(S)-4-{4'-[(4-Butyl-phenylamino)-methyl]-biphenyl-4-sulfonyl}-2,2-dimethyl-thiomorpholine-3-carboxylic acid;
(S)-4-{4'-[(3,4-Dichloro-phenylamino)-methyl]-biphenyl-4-sulfonyl}-2,2-dimethyl-thiomorpholine-3-carboxylic acid;
(S)-4-[4'-(3-Ethoxycarbonyl-piperidin-1-ylmethyl)-biphenyl-4-sulfonyl]-2,2-dimethyl-thiomorpholine-3-carboxylic acid;
(S)-4-[4'-(4-Hydroxy-piperidin-1-ylmethyl)-biphenyl-4-sulfonyl]-2,2-dimethyl-thiomorpholine-3-carboxylic acid;
(S)-4-{4'-[(4-Chloro-3-trifluoromethyl-phenylamino)-methyl]-biphenyl-4-sulfonyl}-2,2-dimethyl-thiomorpholine-3-carboxylic acid;
(S)-4-{4'-[(Furan-2-ylmethyl-methyl-amino)-methyl]-biphenyl-4-sulfonyl}-2,2-dimethyl-thiomorpholine-3-carboxylic acid;
(S)-4-{4'-[((S)-2-Hydroxy-indan-1-yl-amino)-methyl]-biphenyl-4-sulfonyl}-2,2-dimethyl-thiomorpholine-3-carboxylic acid;
(S)-4-(4'-{[(Furan-2-ylmethyl)-amino]-methyl}-biphenyl-4-sulfonyl)-2,2-dimethyl-thiomorpholine-3-carboxylic acid;
(S)-4-(4'-{[2-(2-Methoxy-phenyl)-ethylamino]-methyl}-biphenyl-4-sulfonyl)-2,2-dimethyl-thiomorpholine-3-carboxylic acid;
(S)-2,2-Dimethyl-4-{4'-[(3-methyl-cyclohexylamino)-methyl]-biphenyl-4-sulfonyl}-thiomorpholine-3-carboxylic acid;
(S)-2,2-Dimethyl-4-{4'-[(3-nitro-phenylamino)-methyl]-biphenyl-4-sulfonyl}-thiomorpholine-3-carboxylic acid;
(S)-4-{4'-[(Diisopropylamino)-methyl]-biphenyl-4-sulfonyl}-2,2-dimethyl-thiomorpholine-3-carboxylic acid;
(S)-4-{4'-[(Benzyl-isopropyl-amino)-methyl]-biphenyl-4-sulfonyl}-2,2-dimethyl-thiomorpholine-3-carboxylic acid;
(S)-2,2-Dimethyl-4-(4'-pyrrolidin-1-ylmethyl-biphenyl-4-sulfonyl)-thiomorpholine-3-carboxylic acid;
(S)-4-{4'-[(3-Iodo-phenylamino)-methyl]-biphenyl-4-sulfonyl}-2,2-dimethyl-thiomorpholine-3-carboxylic acid;
(S)-4-{4'-[(4-Methoxy-phenylamino)-methyl]-biphenyl-4-sulfonyl}-2,2-dimethyl-thiomorpholine-3-carboxylic acid;
(S)-4-{4'-[(3-Methoxy-propylamino)-methyl]-biphenyl-4-sulfonyl}-2,2-dimethyl-thiomorpholine-3-carboxylic acid;
(S)-4-{4'-[(2-Hydroxy-ethylamino)-methyl]-biphenyl-4-sulfonyl}-2,2-dimethyl-thiomorpholine-3-carboxylic acid;
(S)-4-(4'-Cyclopentylaminomethyl-biphenyl-4-sulfonyl)-2,2-dimethyl-thiomorpholine-3-carboxylic acid;
(S)-4-[4'-(Isobutylamino-methyl)-biphenyl-4-sulfonyl]-2,2-dimethyl-thiomorpholine-3-carboxylic acid; and
(S)-4-{4'-[(2-Hydroxy-ethylamino)-methyl]-biphenyl-4-sulfonyl}-2,2-dimethyl-thiomorpholine-3-carboxylic acid.

Additional invention compounds bearing various $R^3$ substituent groups are prepared by following the general procedures described above.

(S)-4-(2',4'-Dichloro-biphenyl-4-sulfonyl)-2,2-dimethyl-thiomorpholine-3-carboxylic acid;
(S)-2,2-Dimethyl-4-(4'-trifluoromethyl-biphenyl-4-sulfonyl)-thiomorpholine-3-carboxylic acid;
(S)-2,2-Dimethyl-4-([1,1';4',1"]terphenyl-4"-sulfonyl)-thiomorpholine-3-carboxylic acid;
(S)-4-(4'-Hydroxy-3',5'-dimethyl-biphenyl-4-sulfonyl)-2,2-dimethyl-thiomorpholine-3-carboxylic acid;
(S)-2,2-Dimethyl-4-(3'-trifluoromethyl-biphenyl-4-sulfonyl)-thiomorpholine-3-carboxylic acid;
(S)-4-(3',5'-Dichloro-biphenyl-4-sulfonyl)-2,2-dimethyl-thiomorpholine-3-carboxylic acid;
(S)-4-(2'-Carboxy-biphenyl-4-sulfonyl)-2,2-dimethyl-thiomorpholine-3-carboxylic acid;
(S)-4-(4'-Hydroxy-biphenyl-4-sulfonyl)-2,2-dimethyl-thiomorpholine-3-carboxylic acid;
(S)-4-[4-(1H-Indol-5-yl)-benzenesulfonyl]-2,2-dimethyl-thiomorpholine-3-carboxylic acid;
(S)-2,2-Dimethyl-4-(3'-trifluoromethyl-biphenyl-4-sulfonyl)-thiomorpholine-3-carboxylic acid;
(S)-4-[4-(2,4-Dimethoxy-pyrimidin-5-yl)-benzenesulfonyl]-2,2-dimethyl-thiomorpholine-3-carboxylic acid;
(S)-4-(4'-Amino-biphenyl-4-sulfonyl)-2,2-dimethyl-thiomorpholine-3-carboxylic acid;
(S)-4-[4-(1H-Indol-5-yl)-benzenesulfonyl]-2,2-dimethyl-thiomorpholine-3-carboxylic acid;
(S)-4-(4'-Cyano-biphenyl-4-sulfonyl)-2,2-dimethyl-thiomorpholine-3-carboxylic acid;
(S)-2,2-Dimethyl-4-(4'-trifluoromethyl-biphenyl-4-sulfonyl)-thiomorpholine-3-carboxylic acid;
(S)-2,2-Dimethyl-4-(3'-trifluoromethyl-biphenyl-4-sulfonyl)-thiomorpholine-3-carboxylic acid;
(S)-4-(4'-Hydroxymethyl-biphenyl-4-sulfonyl)-2,2-dimethyl-thiomorpholine-3-carboxylic acid;
(S)-4-(4'-Methoxy-biphenyl-4-sulfonyl)-2,2-dimethyl-thiomorpholine-3-carboxylic acid;

(S)-4-(3'-Isopropyl-biphenyl-4-sulfonyl)-2,2-dimethyl-thiomorpholine-3-carboxylic acid;
(S)-4-(4'-Methanesulfonyl-biphenyl-4-sulfonyl)-2,2-dimethyl-thiomorpholine-3-carboxylic acid;
(S)-4-(4'-Methanesulfonyl-biphenyl-4-sulfonyl)-2,2-dimethyl-thiomorpholine-3-carboxylic acid;
(S)-2,2-Dimethyl-4-(4-pyridin-3-yl-benzenesulfonyl)-thiomorpholine-3-carboxylic acid;
(S)-2,2-Dimethyl-(4-pyridin-4-yl-benzenesulfonyl)-thiomorpholine-3-carboxylic acid;
(S)-2,2-Dimethyl-4-(4'-methyl-biphenyl-4-sulfonyl)-thiomorpholine-3-carboxylic acid;
(S)-4-(4'-Bromo-biphenyl-4-sulfonyl)-2,2-dimethyl-thiomorpholine-3-carboxylic acid;
(S)-2,2-Dimethyl-4-(3'-nitro-biphenyl-4-sulfonyl)-thiomorpholine-3-carboxylic acid;
(S)-2,2-Dimethyl-4-(4-naphthalen-1-yl-benzenesulfonyl)-thiomorpholine-3-carboxylic acid;
(S)-4-(4'-Chloro-biphenyl-4-sulfonyl)-2,2-dimethyl-thiomorpholine-3-carboxylic acid;
(S)-4-(4'-Fluoro-biphenyl-4-sulfonyl)-2,2-dimethyl-thiomorpholine-3-carboxylic acid;
(S)-4-(4'-Formyl-biphenyl-4-sulfonyl)-2,2-dimethyl-thiomorpholine-3-carboxylic acid;
(S)-2,2-Dimethyl-4-(3'-methyl-biphenyl-4-sulfonyl)-thiomorpholine-3-carboxylic acid;
(S)-4-(4-1,3-Benzodioxol-5-yl-benzenesulfonyl)-2,2-dimethyl-thiomorpholine-3-carboxylic acid;
(S)-4-(3'-Chloro-biphenyl-4-sulfonyl)-2,2-dimethyl-thiomorpholine-3-carboxylic acid;
(S)-4-(3'-Formyl-biphenyl-4-sulfonyl)-2,2-dimethyl-thiomorpholine-3-carboxylic acid;
(S)-2,2-Dimethyl-4-(4-naphthalen-2-yl-benzenesulfonyl)-thiomorpholine-3-carboxylic acid;
(S)-4-(3'-Fluoro-biphenyl-4-sulfonyl)-2,2-dimethyl-thiomorpholine-3-carboxylic acid;
(S)-2,2-Dimethyl-4-(4'-methylsulfanyl-biphenyl-4-sulfonyl)-thiomorpholine-3-carboxylic acid;
(S)-2,2-Dimethyl-4-([1,1';4',1"]terphenyl-4"-sulfonyl)-thiomorpholine-3-carboxylic acid;
(S)-4-(2',4'-Difluoro-biphenyl-4-sulfonyl)-2,2-dimethyl-thiomorpholine-3-carboxylic acid;
(S)-2,2-Dimethyl-4-(3'-trifluoromethoxy-biphenyl-4-sulfonyl)-thiomorpholine-3-carboxylic acid;
(S)-4-(2',6'-Dimethoxy-biphenyl-4-sulfonyl)-2,2-dimethyl-thiomorpholine-3-carboxylic acid;
(S)-4-(3'-Methoxy-biphenyl-4-sulfonyl)-2,2-dimethyl-thiomorpholine-3-carboxylic acid;
(S)-4-(3'-Acetyl-biphenyl-4-sulfonyl)-2,2-dimethyl-thiomorpholine-3-carboxylic acid;
(S)-2,2-Dimethyl-4-(4'-phenoxy-biphenyl-4-sulfonyl)-thiomorpholine-3-carboxylic acid;
(S)-4-(3'-Cyano-biphenyl-4-sulfonyl)-2,2-dimethyl-thiomorpholine-3-carboxylic acid;
(S)-4-(2'-Formyl-biphenyl-4-sulfonyl)-2,2-dimethyl-thiomorpholine-3-carboxylic acid;
(S)-4-(3',4'-Difluoro-biphenyl-4-sulfonyl)-2,2-dimethyl-thiomorpholine-3-carboxylic acid;
(S)-4-(3',5'-Difluoro-biphenyl-4-sulfonyl)-2,2-dimethyl-thiomorpholine-3-carboxylic acid;
(S)-4-(2',6'-Difluoro-biphenyl-4-sulfonyl)-2,2-dimethyl-thiomorpholine-3-carboxylic acid;
(S)-4-(3'-Bromo-biphenyl-4-sulfonyl)-2,2-dimethyl-thiomorpholine-3-carboxylic acid;
(S)-4-(2'-Bromo-biphenyl-4-sulfonyl)-2,2-dimethyl-thiomorpholine-3-carboxylic acid;
(S)-4-(2'-Fluoro-biphenyl-4-sulfonyl)-2,2-dimethyl-thiomorpholine-3-carboxylic acid;
(S)-4-(4'-Iodo-biphenyl-4-sulfonyl)-2,2-dimethyl-thiomorpholine-3-carboxylic acid;
(S)-4-(3'-Chloro4'-fluoro-biphenyl-4-sulfonyl)-2,2-dimethyl-thiomorpholine-3-carboxylic acid;
(S)-4-(2',5'-Dichloro-biphenyl-4-sulfonyl)-2,2-dimethyl-thiomorpholine-3-carboxylic acid;
(S)-4-(2'-Acetyl-biphenyl-4-sulfonyl)-2,2-dimethyl-thiomorpholine-3-carboxylic acid;
(S)-4-(3'-Carboxy-biphenyl-4-sulfonyl)-2,2-dimethyl-thiomorpholine-3-carboxylic acid;
(S)-4-(4-Dibenzofuran-1-yl-benzenesulfonyl)-2,2-dimethyl-thiomorpholine-3-carboxylic acid;
(S)-4-(3',4'-Dimethoxy-biphenyl-4-sulfonyl)-2,2-dimethyl-thiomorpholine-3-carboxylic acid;
(S)-2,2-Dimethyl-4-(2',3',4',5',6'-pentafluoro-biphenyl-4-sulfonyl)-thiomorpholine-3-carboxylic acid;
(S)-4-(3'-Amino-biphenyl-4-sulfonyl)-2,2-dimethyl-thiomorpholine-3-carboxylic acid;
(S)-2,2-Dimethyl-4-(4'-vinyl-biphenyl-4-sulfonyl)-thiomorpholine-3-carboxylic acid;
(S)-4-(3'-Ethoxy-biphenyl-4-sulfonyl)-2,2-dimethyl-thiomorpholine-3-carboxylic acid;
(S)-4-(2'-Ethoxy-biphenyl-4-sulfonyl)-2,2-dimethyl-thiomorpholine-3-carboxylic acid;
(S)-4-(4'-Ethoxy-biphenyl-4-sulfonyl)-2,2-dimethyl-thiomorpholine-3-carboxylic acid;
(S)-4-[4-(5-Formyl-thiophen-2-yl)-benzenesulfonyl]-2,2-dimethyl-thiomorpholine-3-carboxylic acid;
(S)-4-(2',5'-Dimethoxy-biphenyl-4-sulfonyl)-2,2-dimethyl-thiomorpholine-3-carboxylic acid;
(S)-4-(2',3'-Dimethyl-biphenyl-4-sulfonyl)-2,2-dimethyl-thiomorpholine-3-carboxylic acid;
(S)-4-(2',5'-Dimethyl-biphenyl-4-sulfonyl)-2,2-dimethyl-thiomorpholine-3-carboxylic acid;
(S)-4-(5'-Fluoro-2'-methoxy-biphenyl-4-sulfonyl)-2,2-dimethyl-thiomorpholine-3-carboxylic acid;
(S)-4-(4'-Isopropyl-biphenyl-4-sulfonyl)-2,2-dimethyl-thiomorpholine-3-carboxylic acid;
(S)-4-(4'-Isopropyl-biphenyl-4-sulfonyl)-2,2-dimethyl-thiomorpholine-3-carboxylic acid;
(S)-4-(5'-Chloro-2'-methoxy-biphenyl-4-sulfonyl)-2,2-dimethyl-thiomorpholine-3-carboxylic acid;
(S)-2,2-Dimethyl-4-(4'-trifluoromethoxy-biphenyl-4-sulfonyl)-thiomorpholine-3-carboxylic acid;
(S)-4-(4'-Hydroxymethyl-biphenyl-4-sulfonyl)-2,2-dimethyl-thiomorpholine-3-carboxylic acid;
(S)-4-(4'-Ethyl-biphenyl-4-sulfonyl)-2,2-dimethyl-thiomorpholine-3-carboxylic acid;
(S)-4-(3'-Formyl-4'-methoxy-biphenyl-4-sulfonyl)-2,2-dimethyl-thiomorpholine-3-carboxylic acid;
(S)-4-(2',5'-Difluoro-biphenyl-4-sulfonyl)-2,2-dimethyl-thiomorpholine-3-carboxylic acid;
(S)-4-(3'-Hydroxymethyl-biphenyl-4-sulfonyl)-2,2-dimethyl-thiomorpholine-3-carboxylic acid;
(S)-4-(4'-tert-Butyl-biphenyl-4-sulfonyl)-2,2-dimethyl-thiomorpholine-3-carboxylic acid;
(S)-2,2-Dimethyl-4-(2'-methyl-biphenyl-4-sulfonyl)-thiomorpholine-3-carboxylic acid;
(S)-4-(3'-Iodo-biphenyl-4-sulfonyl)-2,2-dimethyl-thiomorpholine-3-carboxylic acid;
(S)-2,2-Dimethyl-4-(4-naphthalen-2-yl-benzenesulfonyl)-thiomorpholine-3-carboxylic acid;
(S)-2,2-Dimethyl-4-(4'-methylsulfanyl-biphenyl-4-sulfonyl)-thiomorpholine-3-carboxylic acid;
(S)-4-(2'-Methoxy-biphenyl-4-sulfonyl)-2,2-dimethyl-thiomorpholine-3-carboxylic acid;
(S)-4-[4-(5-Acetyl-thiophen-2-yl)-benzenesulfonyl]-2,2-dimethyl-thiomorpholine-3-carboxylic acid;

(S)-4-[4-(3-Formyl-thiophen-2-yl)-benzenesulfonyl]-2,2-dimethyl-thiomorpholine-3-carboxylic acid;
(S)-4-(4-Benzofuran-2-yl-benzenesulfonyl)-2,2-dimethyl-thiomorpholine-3-carboxylic acid;
(S)-4-[4-(5-Chloro-thiophen-2-yl)-benzenesulfonyl]-2,2-dimethyl-thiomorpholine-3-carboxylic acid;
(S)-4-(4'-Fluoro-3'-methyl-biphenyl-4-sulfonyl)-2,2-dimethyl-thiomorpholine-3-carboxylic acid;
(S)-4-(4-Benzo[b]thiophen-2-yl-benzenesulfonyl)-2,2-dimethyl-thiomorpholine-3-carboxylic acid;
(S)-2,2-Dimethyl-4-[4-(5-methyl-thiophen-2-yl)-benzenesulfonyl]-thiomorpholine-3-carboxylic acid;
(S)-4-(4-Furan-2-yl-benzenesulfonyl)-2,2-dimethyl-thiomorpholine-3-carboxylic acid;
(S)-4-(2'-Fluoro-[1,1';4',1"]terphenyl-4"-sulfonyl)-2,2-dimethyl-thiomorpholine-3-carboxylic acid;
(S)-4-(5'-Isopropyl-2'-methoxy-biphenyl-4-sulfonyl)-2,2-dimethyl-thiomorpholine-3-carboxylic acid;
(S)-2,2-Dimethyl-4-(2'-methylsulfanyl-biphenyl-4-sulfonyl)-thiomorpholine-3-carboxylic acid;
(S)-4-[4-(2-Formyl-thiophen-3-yl)-benzenesulfonyl]-2,2-dimethyl-thiomorpholine-3-carboxylic acid;
(S)-4-(4'-Dimethylamino-biphenyl-4-sulfonyl)-2,2-dimethyl-thiomorpholine-3-carboxylic acid;
(S)-2,2-Dimethyl-4-(3',4',5'-trimethoxy-biphenyl-4-sulfonyl)-thiomorpholine-3-carboxylic acid;
(S)-4-(3'-Isopropyl-biphenyl-4-sulfonyl)-2,2-dimethyl-thiomorpholine-3-carboxylic acid;
(S)-4-(2',4'-Dichloro-biphenyl-4-sulfonyl)-2,2-dimethyl-thiomorpholine-3-carboxylic acid hydroxyamide;
(S)-2,2-Dimethyl-4-(4'-trifluoromethyl-biphenyl-4-sulfonyl)-thiomorpholine-3-carboxylic acid hydroxyamide;
(S)-2,2-Dimethyl-4-([1,1';4',1"]terphenyl-4"-sulfonyl)-thiomorpholine-3-carboxylic acid hydroxyamide;
(S)-4-(4'-Hydroxy-3',5'-dimethyl-biphenyl-4-sulfonyl)-2,2-dimethyl-thiomorpholine-3-carboxylic acid hydroxyamide;
(S)-2,2-Dimethyl-4-(3'-trifluoromethyl-biphenyl-4-sulfonyl)-thiomorpholine-3-carboxylic acid hydroxyamide;
(S)-4-(3',5'-Dichloro-biphenyl-4-sulfonyl)-2,2-dimethyl-thiomorpholine-3-carboxylic acid hydroxyamide;
4'-[(S)-3-Hydroxycarbamoyl-2,2-dimethyl-thiomorpholine-4-sulfonyl]-biphenyl-2-carboxylic acid;
(S)-4-(4"-Hydroxy-biphenyl-4-sulfonyl)-2,2-dimethyl-thiomorpholine-3-carboxylic acid hydroxyamide;
4-[4-(1H-Indol-5-yl)-benzenesulfonyl]-2,2-dimethyl-thiomorpholine-3-carboxylic acid hydroxyamide;
(S)-2,2-Dimethyl-4-(3'-trifluoromethyl-biphenyl-4-sulfonyl)-thiomorpholine-3-carboxylic acid hydroxyamide;
(S)-4-[4-(2,4-Dimethoxy-pyrimidin-5-yl)-benzenesulfonyl]-2,2-dimethyl-thiomorpholine-3-carboxylic acid hydroxyamide;
(S)-4-(4"-Amino-biphenyl-4-sulfonyl)-2,2-dimethyl-thiomorpholine-3-carboxylic acid hydroxyamide;
(S)-4-[4-(1H-Indol-5-yl)-benzenesulfonyl]-2,2-dimethyl-thiomorpholine-3-carboxylic acid hydroxyamide;
(S)-4-(4'-Cyano-biphenyl-4-sulfonyl)-2,2-dimethyl-thiomorpholine-3-carboxylic acid hydroxyamide;
(S)-2,2-Dimethyl-4-(4'-trifluoromethyl-biphenyl-4-sulfonyl)-thiomorpholine-3-carboxylic acid hydroxyamide;
(S)-2,2-Dimethyl-4-(3'-trifluoromethyl-biphenyl-4-sulfonyl)-thiomorpholine-3-carboxylic acid hydroxyamide;
(S)-4-(4'-Hydroxymethyl-biphenyl-4-sulfonyl)-2,2-dimethyl-thiomorpholine-3-carboxylic acid hydroxyamide;
(S)-4-(4'-Methoxy-biphenyl-4-sulfonyl)-2,2-dimethyl-thiomorpholine-3-carboxylic acid hydroxyamide;
(S)-4-(3'-Isopropyl-biphenyl-4-sulfonyl)-2,2-dimethyl-thiomorpholine-3-carboxylic acid hydroxyamide;
(S)-4-(4'-Methanesulfonyl-biphenyl-4-sulfonyl)-2,2-dimethyl-thiomorpholine-3-carboxylic acid hydroxyamide;
(S)-4-(4'-Methanesulfonyl-biphenyl-4-sulfonyl)-2,2-dimethyl-thiomorpholine-3-carboxylic acid hydroxyamide;
(S)-2,2-Dimethyl-4-(4-pyridin-3-yl-benzenesulfonyl)-thiomorpholine-3-carboxylic acid hydroxyamide;
(S)-2,2-Dimethyl-4-(4-pyridin-4-yl-benzenesulfonyl)-thiomorpholine-3-carboxylic acid hydroxyamide;
(S)-2,2-Dimethyl-4-(4'-methyl-biphenyl-4-sulfonyl)-thiomorpholine-3-carboxylic acid hydroxyamide;
(S)-4-(4'-Bromo-biphenyl-4-sulfonyl)-2,2-dimethyl-thiomorpholine-3-carboxylic acid hydroxyamide;
(S)-2,2-Dimethyl-4-(3'-nitro-biphenyl-4-sulfonyl)-thiomorpholine-3-carboxylic acid hydroxyamide;
(S)-2,2-Dimethyl-4-(4-naphthalen-1-yl-benzenesulfonyl)-thiomorpholine-3-carboxylic acid hydroxyamide;
(S)-4-(4'-Chloro-biphenyl-4-sulfonyl)-2,2-dimethyl-thiomorpholine-3-carboxylic acid hydroxyamide;
(S)-4-(4'-Fluoro-biphenyl-4-sulfonyl)-2,2-dimethyl-thiomorpholine-3-carboxylic acid hydroxyamide;
(S)-4-(4'-Formyl-biphenyl-4-sulfonyl)-2,2-dimethyl-thiomorpholine-3-carboxylic acid hydroxyamide;
(S)-2,2-Dimethyl-4-(3'-methyl-biphenyl-4-sulfonyl)-thiomorpholine-3-carboxylic acid hydroxyamide;
(S)-4-(4-1,3-Benzodioxol-5-yl-benzenesulfonyl)-2,2-dimethyl-thiomorpholine-3-carboxylic acid hydroxyamide;
(S)-4-(3'-Chloro-biphenyl-4-sulfonyl)-2,2-dimethyl-thiomorpholine-3-carboxylic acid hydroxyamide;
(S)-4-(3'-Formyl-biphenyl-4-sulfonyl)-2,2-dimethyl-thiomorpholine-3-carboxylic acid hydroxyamide;
(S)-2,2-Dimethyl-4-(4-naphthalen-2-yl-benzenesulfonyl)-thiomorpholine-3-carboxylic acid hydroxyamide;
(S)-4-(3'-Fluoro-biphenyl-4-sulfonyl)-2,2-dimethyl-thiomorpholine-3-carboxylic acid hydroxyamide;
(S)-2,2-Dimethyl-4-(4'-methylsulfanyl-biphenyl-4-sulfonyl)-thiomorpholine-3-carboxylic acid hydroxyamide;
(S)-2,2-Dimethyl-4-([1,1';4',1"]terphenyl-4"-sulfonyl)-thiomorpholine-3-carboxylic acid hydroxyamide;
(S)-4-(2',4'-Difluoro-biphenyl-4-sulfonyl)-2,2-dimethyl-thiomorpholine-3-carboxylic acid hydroxyamide;
(S)-2,2-Dimethyl-4-(3'-trifluoromethoxy-biphenyl-4-sulfonyl)-thiomorpholine-3-carboxylic acid hydroxyamide;
(S)-4-(2',6'-Dimethoxy-biphenyl-4-sulfonyl)-2,2-dimethyl-thiomorpholine-3-carboxylic acid hydroxyamide;
(S)-4-(3'-Methoxy-biphenyl-4-sulfonyl)-2,2-dimethyl-thiomorpholine-3-carboxylic acid hydroxyamide;
(S)-4-(3'-Acetyl-biphenyl-4-sulfonyl)-2,2-dimethyl-thiomorpholine-3-carboxylic acid hydroxyamide;
(S)-2,2-Dimethyl-4-(4'-phenoxy-biphenyl-4-sulfonyl)-thiomorpholine-3-carboxylic acid hydroxyamide;
(S)-4-(3'-Cyano-biphenyl-4-sulfonyl)-2,2-dimethyl-thiomorpholine-3-carboxylic acid hydroxyamide;
(S)-4-(2'-Formyl-biphenyl-4-sulfonyl)-2,2-dimethyl-thiomorpholine-3-carboxylic acid hydroxyamide;
(S)-4-(3',4'-Difluoro-biphenyl-4-sulfonyl)-2,2-dimethyl-thiomorpholine-3-carboxylic acid hydroxyamide;

(S)-4-(3',5'-Difluoro-biphenyl-4-sulfonyl)-2,2-dimethyl-thiomorpholine-3-carboxylic acid hydroxyamide;
(S)-4-(2',6'-Difluoro-biphenyl-4-sulfonyl)-2,2-dimethyl-thiomorpholine-3-carboxylic acid hydroxyamide;
(S)-4-(3'-Bromo-biphenyl-4-sulfonyl)-2,2-dimethyl-thiomorpholine-3-carboxylic acid hydroxyamide;
(S)-4-(2'-Bromo-biphenyl-4-sulfonyl)-2,2-dimethyl-thiomorpholine-3-carboxylic acid hydroxyamide; and
(S)-4-(2'-Fluoro-biphenyl-4-sulfonyl)-2,2-dimethyl-thiomorpholine-3-carboxylic acid hydroxyamide.

The invention compounds of Formula I and Formula III have been evaluated in standard assays for their ability to inhibit the catalytic activity of various MMP enzymes. The assays used to evaluate the biological activity of the invention compounds are well-known and routinely used by those skilled in the study of MMP inhibitors and their use to treat clinical conditions.

The assays measure the amount by which a test compound reduces the hydrolysis of a thiopeptolide substrate catalyzed by a matrix metalloproteinase enzyme. Such assays are described in detail by Ye et al., in *Biochemistry*, 1992;31 (45):11231–11235, which is incorporated herein by reference.

Thiopeptolide substrates show virtually no decomposition or hydrolysis at or below neutral pH in the absence of a matrix metalloproteinase enzyme. A typical thiopeptolide substrate commonly utilized for assays is Ac-Pro-Leu-Gly-thioester-Leu-Leu-Gly-OEt. A 100 μL assay mixture will contain 50 mM of N-2-hydroxyethylpiperazine-N'-2-ethanesulfonic acid buffer ("HEPES") at pH 7.0, 10 mM $CaCl_2$, 100 μM thiopeptolide substrate, and 1 mM 5,5"-dithio-bis-(2-nitro-benzoic acid) (DTNB). The thiopeptolide substrate concentration may be varied from, for example, 10 to 800 μM to obtain Km and Kcat values. The change in absorbance at 405 nm is monitored on a Thermo Max microplate reader (Molecular Devices, Menlo Park, Calif.) at room temperature (22° C.). The calculation of the amount of hydrolysis of the thiopeptolide substrate is based on $E_{412}=13600$ $M^{-1}$ $cm^{-1}$ for the DTNB-derived product 3-carboxy4-nitrothiophenoxide. Assays are carried out with and without matrix metalloproteinase inhibitor compounds, and the amount of hydrolysis is compared for a determination of inhibitory activity of the test compounds.

Several representative compounds have been evaluated for their ability to inhibit various matrix metalloproteinase enzymes. Table I below presents inhibitory activity for compounds from various classes. In Table I, MMP-1FL refers to full length interstitial collagenase; MMP-2FL refers to full length Gelatinase A; MMP-3CD refers to the catalytic domain of stromelysin-1; MMP-7FL refers to full length matrilysin; MMP-9FL refers to full length Gelatinase B; MMP-13CD refers to the catalytic domain of collagenase 3; and MMP-14CD refers to the catalytic domain of MMP-14. Test compounds were evaluated at various concentrations in order to determine their respective $IC_{50}$ values, the micromolar concentration of compound required to cause a 50% inhibition of the catalytic activity of the respective enzyme.

It should be appreciated that the assay buffer used with MMP-3CD was 50 mM of 2-morpholinoethanesulfonic acid monohydrate ("MES") at pH 6.0 rather than the HEPES buffer at pH 7.0 described above.

TABLE I $IC_{50}$ (μM)

| Example No. | MMP-1FL | MMP-2FL | MMP-3CD | MMP-7FL | MMP-9FL | MMP-12CD | MMP-13CD | MMP-14CD |
|---|---|---|---|---|---|---|---|---|
| 1 | 3.1 | 0.006 | 0.003 | 10.0 | 0.26 | —[a] | 0.016 | 0.048 |
| 2 | 0.002 | 0.002 | 0.002 | 0.037 | 0.001 | — | 0.001 | 0.001 |
| 3 | 1.7 | 0.012 | 0.005 | 8.8 | 0.78 | — | 0.032 | 0.059 |
| 4 | 0.005 | 0.001 | 0.003 | 0.031 | 0.004 | — | 0.001 | 0.002 |
| 5 | 1.5 | 0.018 | 0.027 | 10 | 0.063 | — | 0.047 | 0.24 |
| 27 | — | >100 | >100 | — | >100 | — | >100 | — |
| 28 | — | 2.06666 | 2.2 | — | 22.7666 | — | 2.66666 | — |
| 29 | — | >100 | >100 | — | >100 | — | >100 | — |
| 30 | — | 0.042 | 0.01535 | — | 3.6 | — | 0.096 | — |
| 31 | — | >100 | >100 | — | 1.57333 | — | >100 | — |
| 32 | — | 0.1325 | 0.0365 | — | 4.425 | — | 0.145 | — |
| 33 | — | 0.01845 | 0.0148 | — | 3.15 | — | 0.04425 | — |
| 34 | — | 0.18666 | 0.07033 | — | 10.2666 | — | 0.24333 | — |
| 35 | — | 0.035 | 0.01535 | — | 0.479 | — | 0.021 | — |
| 36 | 10.8333 | 0.00635 | 0.0104 | 31.6666 | 0.13 | 0.00113 | 0.01075 | 0.056667 |
| 37 | 2.03333 | 0.0025 | 0.00475 | 6.86666 | 0.069 | 0.001 | 0.00305 | 0.036 |
| 38 | 1.17 | 0.00135 | 0.00295 | 2.66666 | 0.0032 | 0.001 | 0.00145 | 0.034333 |
| 39 | 3.25 | 0.115 | 0.0285 | 25 | 2.785 | 0.013 | 0.16 | 0.67 |
| 40 | 100 | 0.17 | 0.0094 | 13 | 2.2 | 0.004 | 0.1 | 1.5 |
| 41 | 9.7 | 0.23 | 0.054 | 92.5 | 6.65 | 0.0285 | 0.3 | 0.615 |
| 42 | — | 0.16 | 0.02885 | — | 9.15 | — | 0.1135 | — |
| 43 | 7.95 | 0.0023 | 0.0038 | 70 | 0.018 | 0.001 | 0.0033 | 0.16 |
| 44 | — | 0.015 | 0.0088 | — | 0.37 | — | 0.02 | — |
| 45 | 5.75 | 0.0027 | 0.004 | 100 | 0.098 | 0.001 | 00035 | 0.1275 |
| 47 | 5.4 | 0.0061 | 0.0074 | 9 | 0.14 | 0.00125 | 0.01 | — |
| 48 | — | 1.55 | 0.775 | — | 25.85 | — | 2.04 | 0.037 |
| 49 | — | 0.23 | 0.039 | — | 1.5 | — | 0.061 | — |
| 50 | — | 0.024 | 0.019 | — | 1.5 | — | 0.12 | — |
| 51 | — | 0.027 | 0.01 | — | 1 | — | 0.012 | — |
| 52 | — | 0.013 | 0.014 | — | 0.52 | — | 0.036 | — |
| 53 | 3.15 | 0.0043 | 0.0072 | 1.85 | 0.017 | 0.001 | 0.0086 | 0.145 |
| 54 | 11.25 | 0.024 | 0.03 | 100 | 0.17 | 0.0103 | 0.013 | 0.19 |
| 55 | — | 8.8 | 8.9 | — | 59 | — | 7.7 | — |
| 56 | — | 0.81 | 1.5 | — | 18 | — | 1.1 | — |
| 57 | — | 0.0088 | 0.0045 | — | 0.54 | — | 0.013 | — |

TABLE I-continued

| | | | | IC$_{50}$ ($\mu$M) | | | | |
|---|---|---|---|---|---|---|---|---|
| Example No. | MMP-1FL | MMP-2FL | MMP-3CD | MMP-7FL | MMP-9FL | MMP-12CD | MMP-13CD | MMP-14CD |
| 58 | — | 0.1335 | 0.082 | — | 6.3 | — | 0.425 | — |
| 59 | — | 5.2 | 1.1 | — | 30 | — | 5.3 | — |
| 60 | — | 39 | 9.95 | — | 100 | — | 25.5 | — |
| 61 | — | 3.4 | 0.76333 | — | 49 | — | 2.9 | — |
| 62 | — | 6.2 | 0.83 | — | 100 | — | 4.9 | — |
| 63 | — | 68 | 21 | — | 100 | — | 62.5 | — |

[a]"—" means datum not available

The foregoing data establish that the invention compounds of Formula I and Formula III are potent inhibitors of a broad spectrum of MMP enzymes. Because of this potent inhibitory activity, the invention compounds are especially useful to treat diseases mediated by the MMP enzymes, diseases such as cancer, rheumatoid arthritis, osteoarthritis, atherosclerosis, and congestive heart failure.

Administration of a compound of the present invention or a pharmaceutically acceptable salt thereof, to treat the diseases mediated by an MMP enzyme, is preferably, although not necessarily, accomplished by administering the invention compound, or the salt thereof, in a pharmaceutical dosage form.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or Formula III or a corresponding pharmaceutically acceptable salt of a compound of Formula I or Formula II. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 to 1000 mg, preferably 10 to 100 mg according to the particular application and the potency of the active component. The composition can, if desired, also contain other compatible therapeutic agents.

In therapeutic use as agents to inhibit a matrix metalloproteinase enzyme for the treatment of atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon breakdown of connective tissue, the compounds utilized in the pharmaceutical method of this invention are administered at a dose that is effective to inhibit the hydrolytic activity of one or more matrix metalloproteinase enzymes. The initial dosage of about 1 to about 100 mg per kilogram daily will be effective. A daily dose range of about 25 to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 to about 500 mg/kg, and ideally about 25 to about 250 mg/kg, such that it will be an amount which is effective to treat the particular disease being prevented or controlled.

The following examples illustrate typical pharmaceutical compositions provided by the invention.

COMPOSITION EXAMPLE 1

| Tablet Formulation | |
|---|---|
| Ingredient | Amount (mg) |
| Compound of Example 1 | 25 |
| Lactose | 50 |
| Corn starch (for mix) | 10 |
| Corn starch (paste) | 10 |
| Magnesium stearate (1%) | 5 |
| Total | 100 |

The biphenylsulfonamide of Example 1, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of atherosclerosis and arthritis.

COMPOSITION EXAMPLE 2

| Preparation for Oral Solution | |
|---|---|
| Ingredient | Amount |
| Compound of Example 2 | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the biphenylsulfonamide of Example 2 is dissolved therein. The saccharin, sodium benzoate, flavor, and dye are added and dissolved. The volume is adjusted to 100 mL with distilled water. Each milliliter of syrup contains 4 mg of invention compound.

COMPOUND EXAMPLE 3
Parenteral Solution

In a solution of 700 mL of propylene glycol and 200 mL of water for injection is suspended 20 g of the compound of Example 5. After suspension is complete, the pH is adjusted to 6.5 with 1 N sodium hydroxide, and the volume is made up to 1000 mL with water for injection. The formulation is sterilized, filled into 5.0 mL ampoules each containing 2.0 mL , and sealed under nitrogen.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, heart failure, cancer metastasis, tumor angiogenesis, arthritis, and other inflammatory disorders dependent upon tissue invasion by leukocytes.

It should be appreciated that in all invention embodiments described above or in the claims below, whenever an R group such as, for example, $R^1$, $R^2$, $R^3$, $R^4$, $R^5$, or $R^6$, is used more than once to define an invention compound, each use of the R group is independent of any other use of that same R group or, for that matter, any other R group, unless otherwise specified.

What is claimed is:

1. A compound of Formula I

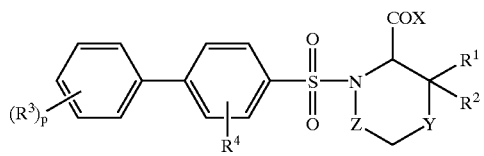

or a pharmaceutically acceptable salt thereof,
wherein:
$R^1$ and $R^2$ independently are hydrogen or $C_1$–$C_6$ alkyl;
Z is $Ch_2$,
each $R^3$ and $R^4$ independently are hydrogen, halo, $C_1$–$C_6$ alkyl, $C_2$–$C_6$ alkenyl, $C_2$–$C_6$ alkynyl; $(CH_2)_m$ OH, $(CH_2)_m$ $OR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m$ $NR^5R^6$, $(CH_2)_m$ $COR^5$, $(CH_2)_m$ $CONR^5R^6$, or $(CH_2)_m$ $CO_2R^5$, $NO_2$, phenoxy, CN, CHO; or two $R^3$ groups on adjacent carbon atoms may be taken together with the carbon atoms to which they are attached to form a ring diradical selected from:

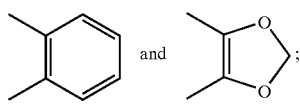

$R^5$ and $R^6$ independently are hydrogen or $C_1$–$C_6$ alkyl, or $R^5$ and $R^6$ taken together with the nitrogen atom to which they are attached complete a 3- to 7-membered ring containing carbon atoms, the nitrogen atom, and optionally 1 heteroatom selected from O, S, and $NR^1$, wherein $R^1$ as defined above;
p is an integer of from 0 to 3;
m is an integer of from 0 to 6;
Y is S, SO, or $SO_2$; and
X is OH;

wherein heterocycle is selected from oxiranyl, pyrrolidinyl, piperidyl, tetrahydropyranyl, morpholinyl, pyrrolidinyl, thiomorpholinyl, piperazinyl, and tetrahydrofuranyl; and heteroaryl is a 5-membered heteroaryl selected from furanyl, pyrrolyl, pyrazolyl, imidazolyl, thiazolyl, isoxazolyl, isothiazolyl, oxazolyl, thiophenyl, and triazolyl, a 6-membered heteroaryl selected from pyridyl and pyrimidinyl, a 9-membered heteroaryl selected from benzothienyl, indolyl, benzotriazolyl, indazolyl, 1,3-benzodioxolyl, indanyl, benzofuranyl, and benzo[b]thiophenyl, or a 13-membered heteroaryl selected from dibenzofuranyl.

2. A compound of Formula II

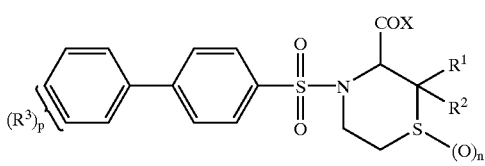

II or a pharmaceutically acceptable salt thereof,
wherein:
Each $R^1$ and $R^2$ independently are hydrogen or $C_1$–$C_6$ alkyl;
each $R^3$ is hydrogen, halo, $C_1$–$C_6$ alkyl, $C_2$–$C_6$ alkenyl, $C_2$–$C_6$ alkynyl, $(CH_2)_m$ OH, $(CH_2)_m$ $OR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m$ $NR^5R^6$, $(CH_2)_m$ $COR^5$, $(CH_2)_m$ $CONR^5R^6$ or $(CH_2)_m$ $CO_2R^5$, $NO_2$, phenoxy, CN, CHO; or two $R^3$ groups on adjacent carbon atoms may be taken together with the carbon atoms to which they are attached to form a ring diradical selected from:

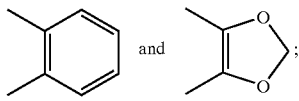

$R^5$ and $R^6$ independently are hydrogen or $C_1$–$C_6$ alkyl, or $R^5$ and $R^6$ taken together with the nitrogen atom to which they are attached complete a 3- to 7-membered ring containing carbon atoms, the nitrogen atom, and optionally 1 heteroatom selected from O, S, and $NR^1$, wherein $R^1$ is as defined above;
m is an integer of from 0 to 6;
p is an integer of from 1 to 5;
n is 0, 1, or 2; and
X is OH;
wherein heterocycle is selected from oxiranyl, pyrrolidinyl, piperidyl, tetrahydropyranyl, morpholinyl, pyrrolidinyl, thiomorpholinyl, piperazinyl, and tetrahydrofuranyl; and
heteroaryl is a 5-membered heteroaryl selected from furanyl, pyrrolyl, pyrazolyl, imidazolyl, thiazolyl, isoxazolyl, isothiazolyl, oxazolyl, thiophenyl, and triazolyl, a 6-membered heteroaryl selected from pyridyl and pyrimidinyl, a 9-membered heteroaryl selected from benzothienyl, indolyl, benzotriazolyl, indazolyl, 1,3-benzodioxolyl, indanyl, benzofuranyl, and benzo[b]thiophenyl, or a 13-membered heteroaryl selected from dibenzofuranyl.

3. The compound of claim 1 wherein $R^1$ and $R^2$ are methyl.
4. The compound of claim 1 wherein $R^3$ is bromo or iodo.
5. The compound of claim 1 wherein $R^4$ is hydrogen.
6. A compound selected from:
(S)-4-(4'-Bromo-biphenyl-4-sulfonyl)-2,2-dimethyl-thiomorpholine-3-carboxylic acid;
(S)-4-(4'-Bromo-biphenyl-4-sulfonyl)-2,2-dimethyl-thiomorpholine-3-carboxylic acid hydroxyamide;
(S)-4-(4'-Bromo-biphenyl-4-sulfonyl)-2,2-dimethyl-1,1-dioxo-thiomorpholine-3-carboxylic acid;
(S)-4-(4'-Bromo-biphenyl-4-sulfonyl)-2,2-dimethyl-1,1-dioxo-thiomorpholine-3-carboxylic acid hydroxyamide;
(S)-4-(4'-Hydroxymethyl-biphenyl-4-sulfonyl)-2,2-dimethyl-thiomorpholine-3-carboxylic acid;
(S)-4-(2'-Carboxy-biphenyl-4-sulfonyl)-2,2-dimethyl-thiomorpholine-3-carboxylic acid;
(S)-4-(4'-Methanesulfonyl-biphenyl-4-sulfonyl)-2,2-dimethyl-thiomorpholine-3-carboxylic acid;
(S)-4-(4'-Formyl-biphenyl-4-sulfonyl)-2,2-dimethyl-thiomorpholine-3-carboxylic acid;
(S)-4-(3'-Formyl-biphenyl-4-sulfonyl)-2,2-dimethyl-thiomorpholine-3-carboxylic acid;
(S)-4-(4'-Dimethylamino-biphenyl-4-sulfonyl)-2,2-dimethyl-thiomorpholine-3-carboxylic acid;
(S)-4-(2'-Bromo-biphenyl-4-sulfonyl)-2,2-dimethyl-thiomorpholine-3-carboxylic acid;
(S)-4-{4'-[(2-Hydroxy-ethylamino)-methyl]-biphenyl-4-sulfonyl}-2,2-dimethyl-thiomorpholine-3-carboxylic acid;
(S)-4-{4'-[(Diisopropylamino)-methyl]-biphenyl-4-sulfonyl}-2,2-dimethyl-thiomorpholine-3-carboxylic acid;
(S)-4-[4'-(Isobutylamino-methyl)-biphenyl-4-sulfonyl]-2,2-dimethyl-thiomorpholine-3-carboxylic acid;
(S)-2,2-Dimethyl-4-(4'-pyrrolidin-1-ylmethyl-biphenyl-4-sulfonyl)-thiomorpholine-3-carboxylic acid;
(S)-4-(4'-Cyclohexylaminomethyl-biphenyl-4-sulfonyl)-2,2-dimethyl-thiomorpholine-3-carboxylic acid;
(S)-2,2-Dimethyl-4-(4'-thiomorpholin-4-ylmethyl-biphenyl-4-sulfonyl)-thiomorpholine-3-carboxylic acid;
(S)-4-(4'-Hydroxymethyl-biphenyl-4-sulfonyl)-2,2-dimethyl-thiomorpholine-3-carboxylic acid hydroxyamide;
(S)-4-(3'-Amino-biphenyl-4-sulfonyl)-2,2-dimethyl-thiomorpholine-3-carboxylic acid hydroxyamide;
(S)-4-(4'-Dimethylamino-biphenyl-4-sulfonyl)-2,2-dimethyl-thiomorpholine-3-carboxylic acid hydroxyamide;
(S)-4-(3'-Bromo-biphenyl-4-sulfonyl)-2,2-dimethyl-thiomorpholine-3-carboxylic acid hydroxyamide;
(S)-2,2-Dimethyl-4-(4'-piperidin-1-ylmethyl-biphenyl-4-sulfonyl)-thiomorpholine-3-carboxylic acid hydroxyamide;
(S)-4-{4'-[(Benzyl-isopropyl-amino)-methyl]-biphenyl-4-sulfonyl}-2,2-dimethyl-thiomorpholine-3-carboxylic acid hydroxyamide;
(S)-2,2-Dimethyl-4-[4'-(4-methyl-piperazin-1-ylmethyl)-biphenyl-4-sulfonyl]-thiomorpholine-3-carboxylic acid hydroxyamide;
(S)-2,2-Dimethyl-4-(4'-piperidin-1-ylmethyl-biphenyl-4-sulfonyl)-thiomorpholine-3-carboxylic acid hydroxyamide;
(S)-4-(4'-Bromo-biphenyl-4-sulfonyl)-2,2-dimethyl-thiomorpholine-3-carboxylic acid;
(S)-2,2-Dimethyl-4-(3'-nitro-biphenyl-4-sulfonyl)-thiomorpholine-3-carboxylic acid;

(S)-2,2-Dimethyl-4-(4-naphthalen-1-yl-benzenesulfonyl)-thiomorpholine-3-carboxylic acid;
(S)-4-(4'-Chloro-biphenyl-4-sulfonyl)-2,2-dimethyl-thiomorpholine-3-carboxylic acid;
(S)-4-(4'-Formyl-biphenyl-4-sulfonyl)-2,2-dimethyl-thiomorpholine-3-carboxylic acid;
(S)-2,2-Dimethyl-4-(3'-methyl-biphenyl-4-sulfonyl)-thiomorpholine-3-carboxylic acid;
(S)-4-(4'-Fluoro-biphenyl-4-sulfonyl)-2,2-dimethyl-thiomorpholine-3-carboxylic acid;
(S)-4-(4-1,3-Benzodioxol-5-yl-benzenesulfonyl)-2,2-dimethyl-thiomorpholine-3-carboxylic acid;
(S)-4-(3'-Chloro-biphenyl-4-sulfonyl)-2,2-dimethyl-thiomorpholine-3-carboxylic acid;
(S)-4-(3'-Formyl-biphenyl-4-sulfonyl)-2,2-dimethyl-thiomorpholine-3-carboxylic acid;
(S)-2,2-Dimethyl-4-(4-naphthalen-2-yl-benzenesulfonyl)-thiomorpholine-3-carboxylic acid;
(S)-2,2-Dimethyl-4-(4'-methylsulfanyl-biphenyl-4-sulfonyl)-thiomorpholine-3-carboxylic acid;
(S)-2,2-Dimethyl-4-([1,1';4',1"]terphenyl-4-sulfonyl)-thiomorpholine-3-carboxylic acid;
(S)-4-(2',4'-Difluoro-biphenyl-4-sulfonyl)-2,2-dimethyl-thiomorpholine-3-carboxylic acid;
(S)-2,2-Dimethyl-4-(4'-phenoxy-biphenyl-4-sulfonyl)-thiomorpholine-3-carboxylic acid;
(S)-4-(3',4'-Difluoro-biphenyl-4-sulfonyl)-2,2-dimethyl-thiomorpholine-3-carboxylic acid;
(S)-4-(3'-Chloro-4'-fluoro-biphenyl-4-sulfonyl)-2,2-dimethyl-thiomorpholine-3-carboxylic acid;
(S)-4-(4'-Ethoxy-biphenyl-4-sulfonyl)-2,2-dimethyl-thiomorpholine-3-carboxylic acid;
(S)-4-(4'-Isopropyl-biphenyl-4-sulfonyl)-2,2-dimethyl-thiomorpholine-3-carboxylic acid;
(S)-2,2-Dimethyl-4-(4'-trifluoromethoxy-biphenyl-4-sulfonyl)-thiomorpholine-3-carboxylic acid;
(S)-4-(4'-Hydroxymethyl-biphenyl-4-sulfonyl)-2,2-dimethyl-thiomorpholine-3-carboxylic acid;
(S)-4-(4'-Ethyl-biphenyl-4-sulfonyl)-2,2-dimethyl-thiomorpholine-3-carboxylic acid;
(S)-4-(3'-Formyl-4'-methoxy-biphenyl-4-sulfonyl)-2,2-dimethyl-thiomorpholine-3-carboxylic acid;
(S)-4-(4'-tert-Butyl-biphenyl-4-sulfonyl)-2,2-dimethyl-thiomorpholine-3-carboxylic acid;
(S)-4-(4'-Fluoro-3'-methyl-biphenyl-4-sulfonyl)-2,2-dimethyl-thiomorpholine-3-carboxylic acid;
(S)-4-(2'-Fluoro-[1,1';4',1"]terphenyl-4"-sulfonyl)-2,2-dimethyl-thiomorpholine-3-carboxylic acid;
(S)-4-(4'-Dimethylamino-biphenyl-4-sulfonyl)-2,2-dimethyl-thiomorpholine-3-carboxylic acid;
(S)-2,2-Dimethyl-4-(3',4',5'-trimethoxy-biphenyl-4-sulfonyl)-thiomorpholine-3-carboxylic acid;
(S)-4-(2',4'-Dichloro-biphenyl-4-sulfonyl)-2,2-dimethyl-thiomorpholine-3-carboxylic acid;
(S)-2,2-Dimethyl-4-(4'-trifluoromethyl-biphenyl-4-sulfonyl)-thiomorpholine-3-carboxylic acid;
(S)-4-(3'-Fluoro-biphenyl-4-sulfonyl)-2,2-dimethyl-thiomorpholine-3-carboxylic acid;
(S)-2,2-Dimethyl-4-(3'-trifluoromethoxy-biphenyl-4-sulfonyl)-thiomorpholine-3-carboxylic acid;
(S)-4-(2',6'-Dimethoxy-biphenyl-4-sulfonyl)-2,2-dimethyl-thiomorpholine-3-carboxylic acid;
(S)-4-(3'-Acetyl-biphenyl-4-sulfonyl)-2,2-dimethyl-thiomorpholine-3-carboxylic acid;
(S)-4-(3'-Cyano-biphenyl-4-sulfonyl)-2,2-dimethyl-thiomorpholine-3-carboxylic acid;
(S)-4-(2'-Formyl-biphenyl-4-sulfonyl)-2,2-dimethyl-thiomorpholine-3-carboxylic acid;
(S)-4-(2'-Fluoro-biphenyl-4-sulfonyl)-2,2-dimethyl-thiomorpholine-3-carboxylic acid; and
(S)-4-(3'-Bromo-biphenyl-4-sulfonyl)-2,2-dimethyl-thiomorpholine-3-carboxylic acid.

7. A compound of Formula III

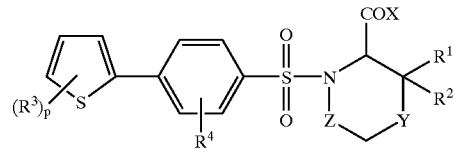

or a pharmaceutically acceptable salt thereof, wherein:

$R^1$ and $R^2$ independently are hydrogen or $C_1$–$C_6$ alkyl;

Z is $CH_2$ each $R^3$ and $R^4$ independently are hydrogen, halo, $C_1$–$C_6$ alkyl, $C_2$–$C_6$ alkenyl, $C_2$–$C_6$ alkynyl, $(CH_2)_m$ OH, $(CH_2)_m$ $OR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle, $(CH_2)_m$ $NR^5R^6$, $(CH_2)_m$ $COR^5$, $(CH_2)_m$ $CONR^5R^6$, or $(CH_2)_m$ $CO_2R^5$, $NO_2$, phenoxy, CN, CHO;

or two $R^3$ groups on adjacent carbon atoms may be taken together with the carbon atoms to which they are attached to form a ring diradical selected from:

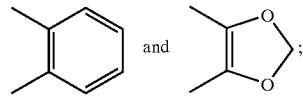

$R^5$ and $R^6$ independently are hydrogen or $C_1$–$C_6$ alkyl, or $R^5$ and $R^6$ taken together with the nitrogen atom to which they are attached complete a 3- to 7-membered ring containing carbon atoms, the nitrogen atom, and optionally 1 heteroatom selected from O, S, and $NR^1$, wherein $R^1$ as defined above;

p is an integer of from 0 to 3;

m is an integer from 0 to 6;

Y is S, SO, or $SO_2$; and

X is OH or NHOH;

wherein heterocycle is selected from oxiranyl, pyrrolidinyl, piperidyl, tetrahydropyranyl, morpholinyl, pyrrolidinyl, thiomorpholinyl, piperazinyl, and tetrahydrofuranyl; and heteroaryl is a 5-membered heteroaryl selected from furanyl, pyrrolyl, pyrazolyl, imidazolyl, thiazolyl, isoxazolyl, isothiazolyl, oxazolyl, thiophenyl, and triazolyl, a 6-membered heteroaryl selected from pyridyl and pyrimidinyl, a 9-membered heteroaryl selected from benzothienyl, indolyl, benzotriazolyl, indazolyl, 1,3-benzodioxolyl, indanyl, benzofuranyl, and benzo[b]thiophenyl, or a 13-membered heteroaryl selected from dibenzofuranyl.

8. A compound of Formula IV

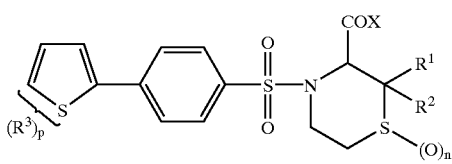

or a pharmaceutically acceptable salt thereof,
wherein:
Each $R^1$ and $R^2$ independently are hydrogen or $C_1$–$C_6$ alkyl;
each $R^3$ independently is hydrogen, halo, $C_1$–$C_6$ alkyl, $C_2$–$C_6$ alkenyl, $C_2$–$C_6$ alkynyl; $(CH_2)_m$ OH, $(CH_2)_m$ $OR^5$, $(CH_2)_m$ cycloalkyl, $(CH_2)_m$ aryl, $(CH_2)_m$ substituted aryl, $(CH_2)_m$ heteroaryl, $(CH_2)_m$ substituted heteroaryl, $(CH_2)_m$ carbocycle, $(CH_2)_m$ heterocycle; $(CH_2)_m$ $NR^5R^6$, $(CH_2)_m$ $COR^5$, $(CH_2)_m$ $CONR^5R^6$, or $(CH_2)_m$ $C_{02}R^5$, $NO_2$, phenoxy, CN, CHO; or two $R^3$ groups on adjacent carbon atoms may be taken together with the carbon atoms to which they are attached to form a ring diradical selected from:

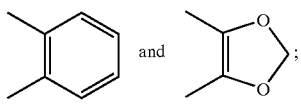

$R^5$ and $R^6$ independently are hydrogen or $C_1$–$C_6$ alkyl, or $R^5$ and $R^6$ taken together with the nitrogen atom to which they are attached complete a 3- to 7-membered ring containing carbon atoms, the nitrogen atom, and optionally 1 heteroatom selected from 0, S, and $NR^1$, wherein $R^1$ is as defined above;
m is an integer from 0to 6;
p is an integer from 1 to 5;
n is 0, 1, or 2; and
X is OH or NHOH;
wherein heterocycle is selected from oxiranyl, pyrrolidinyl, piperidyl, tetrahydropyranyl, morpholinyl, pyrrolidinyl, thiomorpholinyl, piperazinyl, and tetrahydrofuranyl; and
heteroaryl is a 5-membered heteroaryl selected from furanyl, pyrrolyl, pyrazolyl, imidazolyl, thiazolyl, isoxazolyl, isothiazolyl, oxazolyl, thiophenyl, and triazolyl, a 6-membered heteroaryl selected from pyridyl and pyrimidinyl, a 9-membered heteroaryl selected from benzothienyl, indolyl, benzotnazolyl, indazolyl, 1,3-benzodioxolyl, indanyl, benzofuranyl, and benzo[b]thiophenyl, or a 13-membered heteroaryl selected from dibenzofuranyl.

9. The compound of claim 7 wherein $R^1$ and $R^2$ are methyl.

10. The compound of claim 7 wherein X is OH.

11. The compound of claim 7 wherein X is NHOH.

12. The compound of claim 7 wherein $R^3$ is chloro or methyl.

13. The compound of claim 7 wherein $R^4$ is hydrogen.

14. A compound selected from:
(S)-4-[4-(5-Chloro-thiophen-2-yl)-benzenesulfonyly]2,2-dimethyl-thiomorpholine-3-carboxylic acid; and
(S)-2,2-Dimethyl-4-[4-(5-methyl-thiophen-2-yl)-benzenesulfonyl]-thiomorpholine-3-carboxylic acid.

15. A pharmaceutical composition, comprising a compound according to claim 1, or a pharmaceutically acceptable salt thereof, admixed with a pharmaceutically acceptable carrier, diluent, or excipient.

16. A pharmaceutical composition, comprising a compound according to claim 2, or a pharmaceutically acceptable salt thereof, admixed with a pharmaceutically acceptable carrier, diluent, or excipient.

17. A pharmaceutical composition, comprising a compound according to claim 7, or a pharmaceutically acceptable salt thereof, admixed with a pharmaceutically acceptable carrier, diluent, or excipient.

18. A pharmaceutical composition, comprising a compound according to claim 8, or a pharmaceutically acceptable salt thereof, admixed with a pharmaceutically acceptable carrier, diluent, or excipient.

19. A method for inhibiting an MMP enzyme selected from MMP-1, MMP-2, MMP-3, MMP-7, MMP-9, MMP-12, MMP-13, or MMP-14 in an animal, comprising administering to the animal an MMP enzyme inhibiting amount of a compound according to claim 1, or a pharmaceutically acceptable salt thereof, admixed with a pharmaceutically acceptable carrier, diluent, or excipient.

20. A method for inhibiting an MMP enzyme selected from MMP-1, MMP-2, MMP-3, MMP-7, MMP-9, MMP-12, MMP-13, or MMP-14 in an animal, comprising administering to the animal an MMP enzyme inhibiting amount of a compound according to claim 7, or a pharmaceutically acceptable salt thereof, admixed with a pharmaceutically acceptable carrier, diluent, or excipient.

21. A method for treating breast carcinoma, comprising administering to a mammal in need of treatment an anticancer effective amount of a compound of claim 1, or a pharmaceutically acceptable salt thereof.

22. A method for treating a heart failure, comprising administering to a mammal in need of treatment an effective amount of a compound of claim 1, or a pharmaceutically acceptable salt thereof.

23. A method for treating a rheumatoid arthritis, comprising administering to a mammal in need of treatment an effective amount of a compound of claim 1, or a pharmaceutically acceptable salt thereof.

24. A method for treating a osteoarthritis, comprising administering to a mammal in need of treatment an effective amount of a compound of claim 1, or a pharmaceutically acceptable salt thereof.

25. A method for treating breast carcinoma, comprising administering to a mammal in need of treatment an anticancer effective amount of a compound of claim 7, or a pharmaceutically acceptable salt thereof.

26. A method for treating a heart failure, comprising administering to a mammal in need of treatment an effective amount of a compound of claim 7, or a pharmaceutically acceptable salt thereof.

27. A method for treating a rheumatoid arthritis, comprising administering to a mammal in need of treatment an effective amount of a compound of claim 7, or a pharmaceutically acceptable salt thereof.

28. A method for treating a osteoarthritis, comprising administering to a mammal in need of treatment an effective amount of a compound of claim 7, or a pharmaceutically acceptable salt thereof.

* * * * *